United States Patent [19]

Mori et al.

[11] Patent Number: 5,936,130
[45] Date of Patent: *Aug. 10, 1999

[54] PROCESS FOR PREPARING A RHODIUM COMPLEX SOLUTION AND PROCESS FOR PRODUCING AN ALDEHYDE

[75] Inventors: Tomoyuki Mori, Tokyo; Masaki Takai, Kurashiki; Tomohiko Inoue, Kurashiki; Kazuyuki Yokoyama, Kurashiki, all of Japan

[73] Assignee: Mitsubishi Chemical Corporation, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/926,481

[22] Filed: Sep. 10, 1997

[30] Foreign Application Priority Data

Sep. 11, 1996 [JP] Japan .................................. 8-240194
May 23, 1997 [JP] Japan .................................. 9-133288

[51] Int. Cl.⁶ .................................................. C07C 45/50
[52] U.S. Cl. ............................ 568/454; 568/451; 502/24
[58] Field of Search ...................... 568/451, 454; 502/24

[56] References Cited

U.S. PATENT DOCUMENTS

| | | |
|---|---|---|
| 3,641,076 | 2/1972 | Booth . |
| 3,794,671 | 2/1974 | Wilkinson . |
| 3,857,895 | 12/1974 | Booth . |
| 3,968,134 | 7/1976 | Gregorio et al. . |
| 4,021,463 | 5/1977 | Kummer et al. . |
| 4,135,911 | 1/1979 | Balmat . |
| 4,188,363 | 2/1980 | Fell et al. . |
| 4,196,096 | 4/1980 | Dawes et al. . |
| 4,297,239 | 10/1981 | Bryant et al. . |
| 4,340,570 | 7/1982 | Davidson . |
| 4,341,741 | 7/1982 | Davidson et al. . |
| 4,374,278 | 2/1983 | Bryant et al. . |
| 4,388,217 | 6/1983 | Hembre et al. . |
| 4,390,473 | 6/1983 | Cooper . |
| 4,396,551 | 8/1983 | Tsunoda et al. . |
| 4,400,547 | 8/1983 | Dawes et al. . |
| 4,400,549 | 8/1983 | Richter et al. . |
| 4,434,240 | 2/1984 | Pugach . |
| 4,466,074 | 8/1984 | Jamerson et al. . |
| 4,504,588 | 3/1985 | Gärtner et al. . |
| 4,605,780 | 8/1986 | Billig et al. . |
| 4,726,841 | 2/1988 | Grant et al. . |
| 4,731,485 | 3/1988 | Cornils ........................ 568/454 |
| 4,795,727 | 1/1989 | Bach et al. . |
| 4,935,550 | 6/1990 | Miller et al. . |
| 4,944,927 | 7/1990 | Gulliver . |
| 4,945,075 | 7/1990 | Cushman et al. . |
| 4,990,639 | 2/1991 | Bexten et al. . |
| 5,002,914 | 3/1991 | Erpenbach et al. . |
| 5,085,835 | 2/1992 | Weber et al. . |
| 5,091,350 | 2/1992 | Cornils et al. . |
| 5,091,546 | 2/1992 | Lappe et al. . |
| 5,151,537 | 9/1992 | Lappe et al. . |
| 5,206,000 | 4/1993 | Diekhaus et al. . |
| 5,264,600 | 11/1993 | Lappe et al. . |
| 5,294,415 | 3/1994 | Lappe et al. . |
| 5,585,524 | 12/1996 | Sielcken et al. . |
| 5,696,297 | 12/1997 | Kneuper et al. . |

FOREIGN PATENT DOCUMENTS

| | | |
|---|---|---|
| 0 337 262 | 10/1989 | European Pat. Off. . |
| 0 504 814 | 9/1992 | European Pat. Off. . |
| 55-73696 | 6/1980 | Japan . |
| 63-14824 | 1/1988 | Japan . |
| 63-20423 | 1/1988 | Japan . |
| 2-80320 | 3/1990 | Japan . |
| 6-182232 | 7/1994 | Japan . |
| 8-10624 | 1/1996 | Japan . |
| 1 424 818 | 2/1976 | United Kingdom . |
| 1 565 716 | 4/1980 | United Kingdom . |
| 2 075 857 | 11/1981 | United Kingdom . |
| WO 82/01829 | 6/1982 | WIPO . |
| WO 95/25080 | 9/1995 | WIPO . |

OTHER PUBLICATIONS

Derwent Abstracts, Accession No. 82–73694E/198235, JP 57–120598, Jul. 27, 1982.

R. Kummer, et al., Advanced Chemal Separation, vol. 132, No. 19, pp. 19 to 26, "New Hydroformylation Technology with Cobalt Carbonyls", 1974.

*Primary Examiner*—Gary Geist
*Assistant Examiner*—Sreeni Padmanabhan
*Attorney, Agent, or Firm*—Oblon, Spivak, McClelland, Maier & Neustadt, P.C.

[57] ABSTRACT

A process for producing a rhodium complex solution, which comprises contacting an aqueous solution of a water-soluble rhodium compound and an organic solvent solution of a water-insoluble tertiary organic phosphorus compound, preferably in the presence of a $C_{2-8}$ carboxylic acid, in a gas atmosphere containing carbon monoxide, followed by two phase separation, and recovering an organic solvent phase containing a rhodium-tertiary organic phosphorus compound complex. As the above aqueous solution of a rhodium compound, an aqueous solution having rhodium extracted into an aqueous phase from a waste catalyst liquid separated from a hydroformylation reaction step by oxidation treatment in the presence of a recovery accelerator such as a carboxylic acid, an amine, ammonia or an inorganic acid, is used, whereby recycling of rhodium represented by hydroformylation reaction/recovery of the catalyst/regeneration of the catalyst, is made possible, and a cumbersome step of preparing a complex catalyst from an inorganic salt or the like, or a step of preparing a soluble salt from a metal or oxide by combustion in water of the recovered catalyst, can be omitted.

30 Claims, No Drawings

PROCESS FOR PREPARING A RHODIUM COMPLEX SOLUTION AND PROCESS FOR PRODUCING AN ALDEHYDE

The present invention relates to a process for preparing a rhodium complex solution and a process for producing an aldehyde by hydroformylation of an olefin in the presence of a rhodium type complex catalysts. Particularly, it relates to a process for preparing a rhodium-tertiary organic phosphorus compound complex solution from the aqueous solution of a water-soluble rhodium compounds and a process for producing an aldehyde by a hydroformylation reaction of an olefin using such a complex, wherein rhodium is recovered for reuse from a rhodium-containing waste catalyst solution separated from the hydroformylation reaction solution.

A hydroformylation reaction (an oxo reaction) for adding hydrogen and carbon monoxide to an olefinic double bond, is well known as a method for producing an aldehyde or an alcohol. As a catalyst for the hydroformylation reaction, a catalyst containing rhodium, particularly a rhodium-tertiary organic phosphorus compound complex catalyst, is used in many cases for the reason that it is excellent in catalytic activity and selectivity, even though it is rather expensive.

Method for preparation of a rhodium complex solution

As a method for preparing a rhodium complex catalyst to be used for the above hydroformylation reaction, a method wherein the complex is preliminarily prepared and then supplied to the reaction system, or a method wherein a precursor is supplied to the reaction system and converted to the complex in the reaction system, may, for example, be mentioned.

In the method wherein a precursor of the complex is supplied to the reaction system as it is, there is a problem that this precursor will not sufficiently be converted to the effective catalyst, whereby the catalytic activity is rather low. On the other hand, in the method wherein the complex is separately prepared, a separate step is required for the preparation of the complex independently of the reaction. However, the catalytic activity is high, and many proposals have been made for the method of its preparation.

For example, JP-A-47-3320 discloses a process for preparing a rhodium complex, which comprises reacting rhodium (II) acetate with tetrafluoroboric acid and triphenylphosphine, followed by treatment with excess lithium acetate, to obtain a desired rhodium-triphenylphosphine complex. However, this process has drawbacks that an additional agent such as tetrafluoroboric acid or lithium acetate is required, and the operation is cumbersome.

JP-A-55-73696 discloses a process which comprises uniformly dissolving an aqueous rhodium acetate solution and triphenylphosphine in a polar solvent such as methanol or N,N-dimethylformamide, followed by precipitation to obtain a complex. However, a tertiary arylphosphine having no polar substituent, such as triphenylphosphine, has a low solubility in a polar solvent, whereby the yield is low, and the loss of rhodium is so high that the process is hardly useful as an industrial process.

JP-A-57-122023 discloses a method for complexing a rhodium salt of a carboxylic acid in a solvent for a hydroformylation reaction in the presence of a triarylphosphine and water gas. Further, JP-A-8-10624 discloses a method for complexing a water-soluble rhodium compound dissolved in a hydrophilic organic solvent, in the presence of a phosphorus compound. In each of these methods, a rhodium-containing solution obtained by a reaction in a homogeneous phase, is directly introduced into the reaction system which is an organic phase, whereby, for example, when an inorganic salt such as a sulfate is used as the rhodium source, the inorganic salt will enter into the reaction system and may cause a side reaction such as formation of high boiling substances, such being undesirable.

JP-A-63-22046 discloses a method for synthesizing a water-soluble rhodium complex by contacting a rhodium salt of carboxylic acid dissolved in a hydrocarbon, with an aqueous solution containing e.g. a water-soluble phosphine, in the presence of water gas. Such a water-soluble rhodium complex has a low solubility, in many cases, in a solvent in a hydroformylation reaction which is usually carried out in a water-immissible solvent, whereby the reaction tends to be inadequate. Therefore, such a water-soluble rhodium complex can not be regarded as a preferred catalyst.

JP-A-63-14824 discloses a method for extracting a noble metal from an aqueous solution containing the noble metal with a phosphorus type extracting agent in the form of a complex into an organic phase using a monoalkylphosphate as an accelerator, wherein as the phosphorus type extracting agent, a trialkyl phosphonate, a trialkyl phosphate or a trialkyl phosphine oxide is used. However, in this method, a pentavalent phosphorus compound is used, whereby it is impossible to prepare a desired rhodium complex of a water-insoluble tertiary organic phosphorus compound.

Thus, the method wherein the complex is preliminarily separately synthesized has a problem such that the operation is cumbersome, the yield is low, or it is costly.

Recovery of rhodium from a hydroformylation reaction solution

For industrial operation of a hydroformylation reaction by a rhodium catalyst, it is indispensable to recycle the expensive rhodium catalyst for reuse. However, by simple recovery and reuse of the complex catalyst, during repeated use of such a complex catalyst, the catalyst tends to be gradually deactivated by an influence of a catalyst poison which is included in a trace amount from the starting material olefine water gas, etc. Therefore, it is necessary to withdraw the catalyst continuously or intermittently from the reaction system and to supplement a fresh catalyst.

Accordingly, various methods have already been proposed for recovery of rhodium from such a waste catalyst or a deactivated catalyst after reaction.

For example, JP-A-58-116495 discloses a method for producing a hydride carbonyl tris(triorganic phosphorus) rhodium compound by treating a solution having a concentrate of a used hydroformylation reaction solution diluted by an alcohol, with a gas mixture of hydrogen and carbon monoxide, in the presence of an organic phosphorus compound. However, by this method, it is necessary to filtrate the formed rhodium compound, and the operation tends to be cumbersome, and the yield of the rhodium compound is rather low.

European patent (EP)695734 discloses a method which comprises extracting rhodium into an aqueous phase from a hydroformylation reaction solution employing rhodium in the same manner, by means of a water-soluble phosphorus ligand aqueous solution, and treating this aqueous solution with water gas to extract rhodium into an organic solvent. However, in a case where an organic phosphorus compound capable of readily forming a complex with rhodium is present in both an aqueous solution and a water-insoluble organic solution, as in this method, there is a problem such that the recovery of rhodium in the water-insoluble organic solution is rather low.

JP-A-2-145439 discloses a method which comprises subjecting a hydroformylation reaction residue to extraction treatment with an aqueous solution containing a water-soluble phosphine such as triphenylphosphine monosulfonate, to recover rhodium in an aqueous phase. However, this method has a drawback that the water-soluble phosphine is expensive, and the method is applicable only to a limited system.

JP-A-2-284651 discloses a method for extracting and recovering rhodium by a trialkylphosphine such as tributylphosphine from a reaction solution containing a quaternary organic phosphorus compound, acetic acid, etc., obtained from a carbonylation reaction of methanol or the like. However, this method is not intended for extraction from an aqueous solution containing rhodium, and this method is applicable only to a liquid state phosphine compound.

JP-A-54-26218 discloses a method for recovering rhodium from a distillation residue of a hydroformylation reaction using a triarylphosphite as a ligand, wherein 0-valent rhodium is recovered as a precipitate by oxidation by means of oxygen gas. However, in order to regenerate the recovered metal as an active catalyst, cumbersome chemical treatment is required.

JP-A-57-72995 discloses a method wherein an organic solution containing a Group 8 noble metal, is oxidized with air in the presence of a polar organic solvent, water and an alkali, and a metal complex is recovered by precipitation. However, a method of recovering by crystallization or precipitation, like this method, is industrially disadvantageous, since a separate installation for filtration is required.

JP-A-3-146423 discloses a method wherein a distillation residue of a hydroformylation reaction is treated with oxygen gas in the presence of a carboxylic acid and an alkali metal salt of a carboxylic acid, and then extracted with water to recover rhodium. However, in the hydroformylation reaction, inclusion of an alkali metal salt will accelerate formation of high boiling substances. Therefore, when rhodium recovered by the above method is recycled, it is necessary to remove the alkali metal substantially completely in a preliminary stage. However, it is not easy to remove the alkali metal to such an extent that substantially no adverse effect will be given to the reaction system.

U.S. Pat. No. 4,390,473 discloses a method which comprises contacting a solution containing rhodium and cobalt, used as a catalyst in a low pressure hydroformylation, with an aqueous formic acid solution, supplying a gas containing oxygen, followed by phase separation, to recover the metals in an aqueous phase. However, in this method, formic acid practically serves as a reducing agent, whereby rhodium partially separates in the form of a metal, thus leading to a loss of rhodium, such being industrially disadvantageous.

Further, German Patent No. 381203 discloses a method for extracting and recovering metal components contained in a mixed solution of $C_{3-10}$ aliphatic carboxylic acids formed by a hydrocarboxylation reaction of ethylene, by washing with water. However, with respect to a hydroformylation reaction solution containing a water-insoluble phosphorus ligand, rhodium recovery can not be done simply by washing with water, regardless of the presence or absence of a carboxylic acid in the system.

Thus, also in the recovery of rhodium from a hydroformylation reaction solution, there are many problems from the viewpoint of the recovery of rhodium or cumbersomeness of the operation.

Recovery of rhodium from a reaction solution and regeneration and recycling of a catalyst It has been common that rhodium recovered from the hydroformylation reaction solution in the above-described methods, is once converted to metal rhodium or rhodium oxide by e.g. combustion in water, then its water-soluble inorganic salt is prepared, and the inorganic salt is then complexed by the above-mentioned method to prepare a rhodium complex as a catalyst.

Several methods have been proposed in which the above method is simplified, and a complex catalyst is prepared without passing through the conversion to a metal state or to an oxide state from rhodium recovered from the hydroformylation reaction solution.

For example, JP-A-51-63388 discloses a method which comprises treating a distillation residue of a hydroformylation reaction with a mineral acid and hydrogen peroxide to extract contained rhodium or iridium into an aqueous phase, then treating the metal-containing aqueous solution with carbon monoxide in the presence of a tertiary phosphine and a hydrogen halide acid or a alkali halide, and recovering the generated complex by precipitation. In this method, a halide is used, and a halogen-resistant material has to be used for the apparatus, and this method is disadvantageous from the viewpoint of the installation cost. Further, in a case where a non-halogen type catalyst system is to be used, this method can not be applied, since the halogen causes deactivation of the catalyst.

Further, JP-A-2-48419 discloses a method which comprises reacting a distillation residue of a hydroformylation reaction with an oxidizing agent, followed by contacting with an aqueous solution containing e.g. a water-soluble phosphine in the presence of water gas, to extract the rhodium complex in the aqueous solution. Like the above-mentioned method disclosed in JP-A-63-22046, this method is a method wherein a water-soluble rhodium complex is prepared in an aqueous solution. Accordingly, this method has a problem that in a hydroformylation reaction which is carried out in an organic medium, the solubility of the water-soluble catalyst in the organic medium is low, and the reactivity is accordingly low.

As described above, many proposals have been made with respect to a method for recovering rhodium from a hydroformylation reaction solution and reusing it as a catalyst. However, none of them is fully satisfactory for industrial application.

Accordingly, it is an object of the present invention to overcome the drawbacks of the prior art and to provide a method for efficiently recovering rhodium for reuse from a hydroformylation reaction solution containing rhodium.

The present inventors have found it possible to accomplish the above object by using the methods disclosed in the following items and have completed the present invention. That is, the present invention resides in the following:

1. A process for preparing a rhodium complex solutions which comprises contacting an aqueous solution of a water-soluble rhodium compound and an organic solvent solution of a water-insoluble tertiary organic phosphorus compound in a gas atmosphere containing carbon monoxide, followed by phase separations and recovering an organic solvent phase containing a rhodium-tertiary organic phosphorus compound complex.

2. The process for preparing a rhodium complex solution according to Item 1 wherein the step of contacting an aqueous solution of a water-soluble rhodium compound and an organic solvent solution of a water-insoluble tertiary organic phosphorus compound in a gas atmosphere containing carbon monoxide, is carried out in the presence of a $C_{2-8}$ carboxylic acid as a complexing accelerator.

3. The process for preparing a rhodium complex solution according to Item 1 or 2, wherein the water-soluble rhodium compound is an inorganic acid salt of rhodium.

4. The process for preparing a rhodium complex solution according to Item 1 or 2, wherein the water-soluble rhodium compound is a rhodium salt of a $C_{2-8}$ carboxylic acid.

5. The process for preparing a rhodium complex solution according to any one of Items 1 to 4, wherein the aqueous solution of a water-soluble rhodium compound is a rhodium-containing aqueous solution separated from a hydroformylation reaction solution of an olefin.

6. The process for preparing a rhodium complex solution according to Item 5, wherein the aqueous solution of a water-soluble rhodium compound is a rhodium-containing aqueous solution obtained by treating a rhodium-containing solution separated from the hydroformylation reaction solution of an olefin, with an oxidizing agent in the presence of a recovery accelerator and an aqueous medium.

7. The process for preparing a rhodium complex solution according to Item 6, wherein the recovery accelerator is at least one member selected from the group consisting of (A) a $C_{2-8}$ carboxylic acid, (B) an amine or an amine salts (C) ammonia or an ammonium salt, and (D) an alkali metal salt of an inorganic acid.

8. The process for preparing a rhodium complex solution according to Item 7, wherein a $C_{2-8}$ carboxylic acid is used as the recovery accelerator, and it is used also as the complexing accelerator without being removed.

9. The process for preparing a rhodium complex solution according to Item 8, wherein the carboxylic acid is acetic acid.

10. The process for preparing a rhodium complex solution according to any one of Items 1 to 9, wherein the water-insoluble tertiary organic phosphorus compound is a triarylphosphine.

11. The process for preparing a rhodium complex solution according to any one of Items 1 to 10, wherein the gas containing carbon monoxide is a gas mixture of hydrogen and carbon monoxide (water gas), and its pressure is within a range of atmospheric pressure to 300 $kg/cm^2$.G.

12. A process for producing an aldehyde by hydroformylating a compound having an olefinic unsaturated bond with carbon monoxide and hydrogen in the presence of a rhodium complex in a water-insoluble solvent, which comprises:

1) a waste catalyst separation step of separating a rhodium-containing liquid from a hydroformylation reaction step, 2) an oxidation/extraction step of subjecting the rhodium-containing liquid to oxidation treatment in the presence of an aqueous medium containing a recovery accelerator to extract rhodium into an aqueous phase, 3) a rhodium-containing aqueous phase separation step of separating the aqueous phase from an organic phase, 4) a complexing step of contacting the aqueous phase containing rhodium, with an organic solvent solution of a water-insoluble tertiary organic phosphorus compound, in a gas atmosphere containing carbon monoxide, to extract rhodium in the form of a tertiary organic phosphorus compound complex into the organic solvent, 5) a rhodium complex separation step of separating the organic phase from the aqueous phases, and 6) a recycling step of recycling the organic phase containing the rhodium-tertiary organic phosphorus compound complex to the above-mentioned hydroformylation step.

13. The process for producing an aldehyde according to Item 12, wherein the aqueous phase separated from the organic phase containing the rhodium-tertiary organic phosphorus compound complex, is supplied to the oxidation/extraction step.

14. The process for producing an aldehyde according to Item 12 or 13, wherein the recovery accelerator is at least one member selected from the group consisting of (A) a $C_{2-4}$ carboxylic acid, (B) an amine or an amine salt, and (C) ammonia or an ammonium salt.

15. The process for producing an aldehyde according to any one of Items 12 to 14, wherein oxygen or an oxygen-containing gas is used for the oxidation treatment in the oxidation/extraction step.

16. The process for producing an aldehyde according to any one of Items 12 to 15, wherein the water-insoluble tertiary organic phosphorus compound used in the complexing step, is a triarylphosphine.

17. The process for producing an aldehyde according to any one of Items 12 to 16, wherein the gas containing carbon monoxide used in the complexing step, is water gas.

18. The process for producing an aldehyde according to Item 17, wherein the pressure of the water gas is within a range of atmospheric pressure to 300 $kg/cm^2$.G.

19. A process for recovering rhodium, which comprises contacting a rhodium-containing solution used for a hydroformylation reaction, with an oxidizing agent and an aqueous medium containing at least one recovery accelerator selected from the group consisting of (A) a $C_{2-4}$ carboxylic acid, (B) an amine or an amine salt, (C) ammonia or an ammonium salt, and (D) an alkali metal salt of an inorganic acid, followed by phase separation, and recovering an aqueous phase containing rhodium.

20. The process for recovering rhodium according to Item 19, wherein the $C_{2-4}$ carboxylic acid is an aliphatic monocarboxylic acid or dicarboxylic acid.

21. The process for recovering rhodium according to Item 19 or 20, wherein the $C_{2-4}$ carboxylic acid is acetic acid.

22. The process for recovering rhodium according to Item 19, wherein the inorganic acid is at least one acid selected from the group consisting of sulfuric acid, nitric acid, hydrochloric acid, carbonic acid, phosphoric acid and boric acid, and the alkali metal is sodium or potassium.

23. The process for recovering rhodium according to Item 19, wherein the amine is an aliphatic amine having a polar substituent.

24. The process for recovering rhodium according to Item 19, wherein the amine is a heterocyclic amine.

25. The process for recovering rhodium according to Item 19, wherein the ammonium salt is an ammonium salt of an aliphatic carboxylic acid or an aromatic carboxylic acid 26. The process for recovering rhodium according to Item 19, wherein the ammonium salt is an ammonium salt of an inorganic acid.

27. The process for recovering rhodium according to any one of Items 19 to 26, wherein the volume ratio of the aqueous medium to the rhodium-containing solution is from 0.1 to 10.

28. The process for recovering rhodium according to any one of Items 19 to 27, wherein the oxidizing agent is oxygen or an oxygen-containing gas.

29. The process for recovering rhodium according to any one of Items 19 to 27, wherein the oxidizing agent is an inorganic peroxide or an organic peroxide.

30. The process for recovering rhodium according to any one of Items 19 to 29, wherein the rhodium-containing solution used for the hydroformylation reactions is a solution obtained by subjecting a $C_{2-20}$ olefinic hydrocarbon to hydroformylation in the presence of a rhodium complex compound and an organic phosphorus compound and then removing the majority of the aldehyde product and the organic phosphorus compound.

Now, the present invention will be described in detail with reference to the preferred embodiments.

Method for preparing a rhodium complex solution

The water-soluble rhodium compound to be used in the process of the present invention may, for example, be an inorganic acid salt, an organic acid salt or a complex salt of rhodium. Specifically, it may, for example, be an inorganic acid salt such as rhodium chloride, rhodium bromide, rhodium nitrate, rhodium sulfate or rhodium phosphate, a complex salt such as chloropentaammine rhodium chloride ([$RhCl(NH_3)_5]Cl_2$) or hexaammine rhodium acidic nitrate ([$Rh(NH_3)_6](NO_3)$), an organic acid salt such as rhodium formate, rhodium acetate, rhodium propionate or rhodium 2-ethylhexanoate, or hexachlororhodium acid ($H_3[RhCl_6]$). Preferred are an inorganic acid salt of rhodium such as rhodium chloride, rhodium sulfate or rhodium nitrate, and a $C_{2-8}$ carboxylic acid salt of rhodium such as rhodium acetate or rhodium propionate. More preferred is rhodium acetate.

Some of these compounds may be available in the form of an aqueous solution. However, it is usual to use a solid rhodium compound by dissolving it in water.

Further, a rhodium-containing aqueous solution recovered from a solution of a reaction such as a hydroformylation reaction, a hydrogenation reaction or a carbonylation reaction, may also be used in the process of the present invention. Such a rhodium-containing aqueous solution may, for example, be one obtained by extracting the above reaction solution directly with an aqueous medium, or one obtained by concentrating the reaction solution, followed by extraction with an aqueous medium, or it may be a rhodium-containing aqueous solution obtained by subjecting such a reaction solution to oxidation treatment, followed by extraction with an aqueous medium. Preferably, it is a rhodium-containing aqueous solution recovered from a rhodium-containing liquid used as a catalyst solution for a hydroformylation reaction of an olefin, more preferably an aqueous solution obtained by treating a rhodium-containing liquid separated from a reaction solution of hydroformylation of an olefin in a water-insoluble solvent, with an oxidizing agent in the presence of an aqueous medium, preferably in the presence of a recovery accelerator, to extract rhodium in water.

Such recovery of rhodium from a hydroformylation reaction solution will be described in detail hereinafter.

In a rhodium aqueous solution oxidized and recovered in the presence of a recovery accelerator as mentioned above, the recovery accelerator remains in many cases. Depending upon the type, such a recovery accelerator may accelerate preparation of a rhodium complex solution of the present invention (a complexing accelerator), but some may adversely affect the preparation.

For example, presence of a carboxylic acid improves the recovery of a rhodium complex as described hereinafter. On the other hand, in a case where a polar nitrogen-containing compound or tertiary organic phosphorus compound capable of readily forming a water-soluble complex with rhodium is present in the aqueous solution, a coordination equilibrium will be formed between the tertiary organic phosphorus compound in the water-insoluble organic solution as an extracting solvent and the coordinating compound in such an aqueous solution, whereby the recovery of the rhodium complex recovered in the organic solvent tends to be low, such being undesirable.

Such a nitrogen-containing compound may, for example, be an aminee ammonia or an ammonium salt. Accordingly, when an amine, ammonia or an ammonium salt is used as the above recovery accelerator, it is necessary to minimize the amount of the amine remaining in the aqueous solution of the rhodium compound after extraction. The polar tertiary organic phosphorus compound capable of readily forming a complex with rhodium may, for example, be a sulfonated or carboxylated phosphinee such as trisulfonated triphenylphosphine or its salt, monosulfonated triphenylphosphine or its salt, tricarboxylated triphenylphosphine or its salt, dibisphenylphosphinoethane monosulfonate or its salt, or a phosphite compound. It is not desirable that such a polar tertiary organic phosphorus compound remains in the aqueous solution of the water-soluble rhodium compound.

The concentration of the rhodium compound in the aqueous solution is not particularly limited so long as the resulting complex is soluble in an organic solvent. However, it is usually from 1 to 10,000 ppm, preferably from 10 to 1,000 ppm, as calculated as rhodium metal.

The aqueous solution of the rhodium compound may contain a polar solvent such as a $C_{1-4}$ alkanol such as methanol, ethanol or propanol, a glycol such as ethylene glycol, ethylene glycol monomethyl ether or diethylene glycol dimethyl ether, or an alkyl ether thereof, in a range not to impair formation of two phases with an organic solvent solution to be contacted. The amount of such a polar solvent in the aqueous solution is not particularly limited so long as two phases are formed with the organic solvent to be contacted, but it is usually from 0 to 50 wt %.

In the process of the present invention, the aqueous solution of the water-soluble rhodium compound and the organic solvent solution of the water-insoluble tertiary organic phosphorus compound are contacted in a gas atmosphere containing carbon monoxide, followed by two phase separation, to recover the organic solvent phase containing a rhodium-tertiary organic phosphorus compound complex.

Here, it is possible to improve the recovery of the rhodium-tertiary organic phosphorus compound complex by the presence of a $C_{2-8}$ carboxylic acid as a complexing accelerator when the aqueous solution of the water-soluble rhodium compound and the organic solvent solution of the water-insoluble tertiary organic phosphorus compound are contacted. The $C_{2-8}$ carboxylic acid to be used as such a complexing accelerator, may, for example, be an aliphatic mono or dicarboxylic acid such as acetic acid, propionic acid, butyric acid, valeric acid, 2-ethylhexanoic acid, oxalic acid, maronic acid, malic acid, glycolic acid, lactic acid or hydroxybutyric acid, or a mixture thereof. Preferred is a $C_{2-4}$ monocarboxylic acid, and more preferred is acetic acid. Such a carboxylic acid is usually added to the rhodium aqueous solution, but it may be added to the organic solvent.

As described hereinafter, such a carboxylic acid is effective also as a recovery accelerator in a case where a water-soluble rhodium compound is extracted in an aqueous medium by oxidation treatment in the presence of the aqueous medium containing a catalyst-containing liquid separated from a carbonylation reaction solutions.

Accordingly, in a preferred embodiment of the process of the present invention, a rhodium-containing aqueous solution obtained by subjecting a rhodium-containing liquid separated from a reaction solution from a hydroformylation reaction in a non-aqueous medium, to oxidation treatment in an aqueous medium using a $C_{2-8}$ carboxylic acid as a recovery accelerator, is used for the complexing step without removing the carboxylic acid out of the system.

Further, as mentioned above, an amine or an ammonium salt is likely to form a water-soluble complex with rhodium whereby the recovery of the desired rhodium complex is likely to deteriorate. In such a case where a nitrogen-containing compound is present, it is possible to improve the recovery of the rhodium complex by adding a carboxylic acid.

The effect of a carboxylic acid for improving the recovery is particularly remarkable when a rhodium-containing aqueous solution recovered from a hydroformylation reaction solution is used as the aqueous solution of a water-soluble rhodium compound. The concentration of a carboxylic acid in such a rhodium-containing aqueous solution is usually from 3 to 50 wt %, preferably from 20 to 40 wt %.

The water-insoluble tertiary organic phosphorus compound to be used in the present invention may be one having a low solubility in the rhodium aqueous solution to be used and a high solubility in an organic solvent. As such a tertiary organic phosphorus compound, phosphine or phosphite may, for example, be mentioned. A preferred phosphine compound may, for example, be a triarylphosphine such as triphenylphosphine, tritoluylphosphine or trixylylphosphine, an alkylarylphosphine such as propyldiphenylphosphine or dipropylphenylphosphine, an alkylphosphine such as tributylphosphine, trioctylphosphine or tirbenzylphosphine, or a triaralkylphosphine. A preferred phosphite compound may, for example, be a triarylphosphite such as triphenylphosphite, or a phosphite having a low hydrolyzability due to a steric hindrance, such as tris(o-tert-butylphenyl)phosphite. Among them, a triarylphosphine is preferred.

These phosphine and phosphite compounds may be used in combination as a mixture. Further, in a case where a water-insoluble tertiary organic phosphorus compound is used for a reaction where a rhodium complex solution is used as a catalyst, it is preferred to employ the same organic phosphorus compound.

The amount of such a water-insoluble tertiary organic phosphorus compound is at least an amount sufficient to form a mono- or di-coordinated complex with rhodium in the aqueous rhodium solution, and it is usually used in a large excess amount. The concentration of the water-insoluble tertiary organic phosphorus compound in the organic solvent is usually from 0.1 to 50 wt % preferably from 0.5 to 30 wt %.

The organic solvent to be used in the process of the present invention may be any organic solvent so long as it is capable of forming two phases with the above-mentioned aqueous solution and it is capable of dissolving the tertiary organic phosphorus compound and the resulting complex. Specifically, it may, for example, be an aliphatic saturated hydrocarbon such as hexane or heptane, an aromatic hydrocarbon such as benzene, toluene or xylene, an aliphatic unsaturated hydrocarbon such as hexene, octene or nonene, an ester such as ethyl acetate, a ketone such as methyl isobutyl ketone, an aldehyde such as butyraldehyde, valeraldehyde, nonylaldehyde or decylaldehyde, or a mixture thereof. Otherwise, it may be a solvent for a reaction wherein the rhodium complex catalyst is used, the reaction mixture itself, or its concentrated product. Preferably, it is a solvent in which a reaction is carried out by using this catalyst, the reaction solution or an organic hydrocarbon.

The ratio of the aqueous solution to the organic solution to be contacted is within a range of from 0.1 to 10, preferably from 1 to 5, in a volume ratio of aqueous phase/oil phase (organic phase).

The process of the present invention is carried out in a gas atmosphere containing carbon monoxide. The effect of the carbon monoxide-containing gas is not clearly understood. However, it is believed that such a gas accelerates complexing to a complex which is readily soluble in an organic solvent. Namely, a water-soluble rhodium compound is a trivalent rhodium compound in many cases, and it is considered that such a rhodium compound is reduced by carbon monoxide gas to form a monovalent rhodium complex, and a carbonyl complex is formed by coordination of carbon monoxide, whereby dissolution in the organic solvent is accelerated, and the extraction is improved. Further, by the treatment with the carbon monoxide-containing gas, it is possible to obtain a complex having excellent activity as a catalyst in a carbonylation reaction such as a hydroformylation reaction. As the carbon monoxide-containing gas which can be used in the present invention, carbon monoxide gas or water gas may be mentioned. Among them, water gas is preferred. The volume ratio of hydrogen to carbon monoxide gas in such water gas may be at any level within a range of from 0.1 to 10. More preferably, it is a gas mixture comprising hydrogen and carbon monoxide in a ratio of 1:1. Further, the carbon monoxide-containing gas is preferably used under pressure. The pressure is preferably within a range of from atmospheric pressure to 300 $kg/cm^2.G$, preferably from 5 to 100 $kg/cm^2.G$, more preferably from 10 to 50 $kg/cm^2.G$.

The temperature for the contacting treatment is usually from room temperature to 200° C., preferably from 80 to 150° C., more preferably from 120 to 140° C.

The time for contacting treatment is not particularly limited. However, the treatment is carried out for a sufficient time so that rhodium is adequately extracted into the organic solvent, and it is usually from 0.5 to 2 hours.

The reaction system may be a batch system, a semi batch system where the gas is circulated, or a continuous system. This reaction is a three phase reaction of gas-liquid-liquid, and it is desirable that these three phases are sufficiently contacted. So long as contact of these three phases can be sufficiently carried out, any reactor such as an agitation tank, a packed type or plate column type countercurrent or concurrent continuous extraction column, or a static mixer, may be employed.

After the treatment under carbon monoxide gas, by the phase separation, the organic solvent phase containing a rhodium complex is recovered and recycled as a catalyst to the hydroformylation step.

On the other hand, the aqueous phase after separating the organic solvent phase, contains the accelerator, and can be recycled to the oxidation treatment step for reuse. In such a case, the entire amount may be re-used. However, to prevent accumulation of undesirable components, a part thereof may be continuously or intermittently purged, and an accelerator may be supplemented to keep the concentration of the accelerator to be constant.

Recovery of rhodium from a hydroformylation reaction solution

As mentioned above, as the rhodium-containing aqueous solution to be used for preparation of the rhodium complex solution of the present invention, it is preferred to employ one recovered from a hydroformylation reaction solution.

More preferred is one obtained by treating a rhodium-containing liquid with an oxidizing agent in the presence of a recovery accelerator and an aqueous medium.

Here, the recovery accelerator is a water-soluble substance which accelerates the reaction wherein rhodium in a rhodium-containing liquid recovered from a hydroformylation reaction solution is subjected to oxidation treatment to extract it into an aqueous medium. Specifically, it may, for example, be a $C_{2-8}$ carboxylic acid such as acetic acid, propionic acid or oxalic acid, an amine such as monomethanolamine, monoethanolamine, diethanolamine, trimethanolamine, or ethylenediamine, or an amine salt such as an organic acid salt or an inorganic acid salt of such an amine, ammonia, or an ammonium salt of an organic acid or an inorganic acid such as ammonium acetate or ammonium chloride, an inorganic acid such as sulfuric acid, nitric acid, hydrochloric acid, carbonic acid, boric acid or phosphoric acid, or an alkali metal salt of such an inorganic acid.

The $C_{2-8}$ carboxylic acid may, for example, be a mono- or di-carboxylic acid such as acetic acid, propionic acid, butyric acid, oxalic acid, maronic acid, malic acid, glycolic acid, lactic acid or hydroxybutyric acid, or a mixture thereof.

The concentration of the carboxylic acid in the aqueous medium is usually from 5 to 50 wt %, preferably from 20 to 40 wt %.

As the amine, an aliphatic amine, an aromatic amine or a heterocyclic amine, which is soluble in the aqueous medium, may be used. Among these amines, preferred is an amine which shows a large distribution into the aqueous solution when contacted with the rhodium-containing liquid. An amine having a polar functional group such as a hydroxyl group, an amino group or a cyano group as a substituent on nitrogen, is preferred. Particularly preferred are alkanolamines or diamines. Specific examples of alkanolamines include methanolamine, ethanolamine, propanolamine, butanolamine, methylethanolamine, dimethylethanolamine, dimethanolamine, diethanolamine, dipropanolamine, trimethanolamine, triethanolamine, and tripropanolamine. Specific examples diamines include ethylenediamine, and tetramethylethylenediamine. In addition to the above aliphatic amines, amines which can be used in the present invention may, for example, an aromatic amine such as aniline, or a heterocyclic amine such as pyridine, pyrrole, imidazole or oxazole.

The amine salt may be selected from an organic acid salt and an inorganic acid salt of an aliphatic amine such as methylamine, ethylamine, triethylamine, ethanolamine, or ethylenediamine, an aromatic amine such as aniline, or a heterocyclic amine such as pyridine or pyrrole. The organic acid salt is a salt of an aliphatic mono- or di-carboxylic acid, or a salt of an aromatic carboxylic acid. The useful carboxylic acid is a $C_{2-8}$ mono- or di-carboxylic acid such as acetic acid, propionic acid, butyric acid, valeric acid, octylic acid, oxalic acid, maronic acid, malic acid, glycolic acid, lactic acid or hydroxybutyric acid. The inorganic acid salt is a salt of e.g. sulfuric acid or nitric acid. Further, the amine salt may be formed in the system. For example, the above acid and the amine are separately added to prepare the amine salt in the system, or in a case where an organic acid or an inorganic acid is already present in the hydroformylation reaction solution, an amine may be added to form a salt. The concentration of an amine or an amine salt in the aqueous medium is from 0.01 to 10 mol/l, preferably from 0.1 to 5 mol/l.

The ammonium salt may be selected from an organic acid salt and an inorganic acid salt soluble in the aqueous medium.

The organic acid salt may be the same salt of an organic acid as mentioned above with respect to the amine salt. The inorganic acid salt may be a salt of sulfuric acid, nitric acid, hydrochloric acid, carbonic acid, boric acid or phosphoric acid.

The concentration of ammonia or an ammonium salt in the aqueous medium is usually from 0.01 to 10 mol/l, preferably from 0.1 to 5 mol/l. Ammonia may be aqueous ammonia or may be fed in a gas state, or aqueous ammonia and gaseous ammonia may be used in combination. The ammonium salt may be formed in the system from an acid and ammonia.

As the inorganic acid or the inorganic acid salt, sulfuric acid, nitric acid, hydrochloric acid, carbonic acid, boric acid or phosphoric acid, or an alkali metal salt thereof may be mentioned. Preferred is a sulfate or a carbonate. The concentration of the inorganic acid salt in the aqueous medium is usually from 0.01 to 10 mol/l, preferably from 0.1 to 5 mol/l.

Further, the aqueous medium used here, is water, or a mixed liquid of water and a polar organic solvent. In the case of a mixed solvent, the content of the polar organic solvent is determined so that water and the polar organic solvent mixed thereto constitute a homogeneous phase, and separate from the phase of the rhodium-containing catalyst solution. The polar organic solvent which is mixed with water, may, for example, be a ketone such as acetone, methyl ethyl ketone, 2-pentanone, 3-pentanone or diethyl ketone, an alcohol such as methanol, ethanol, propanol, butanol or ethylene glycol, or an ether such as diethyl ether, dipropyl ether, tetrahydrofuran, dioxane, diglyme or triglyme. Preferred is methanol, ethanol or propanol. As the aqueous medium, it is preferred to employ water.

The amount of the aqueous medium containing the recovery accelerator is usually from 0.1 to 10 times by volume, preferably from 0.5 to 4 times by volume, to the rhodium-containing liquid to be treated.

The oxidizing agent to be used for the oxidation treatment is selected from an inorganic peroxide such as hydrogen peroxide, an organic peroxide such as t-butyl peroxide or octene peroxide, and oxygen or an oxygen-containing gas. Preferably, it is hydrogen peroxide, or oxygen or an oxygen-containing gas. Particularly preferred is oxygen-containing gas. The concentration of oxygen in the oxygen-containing gas may optionally be selected, and one obtained by diluting oxygen with an inert gasg may be used. For industrial purposes it is advantageous to use air.

The feeding system of the oxygen-containing gas is not particularly limited, and may be a batch system or a continuous system. The required amount of oxygen is determined by the amount of rhodium in the rhodium-containing liquid, and the amount of the ligand or the organic substance oxidized. Therefore, the amount may be in excess of such the required amount. Further, the recovery depends not only on the total amount of oxygen but also on its partial pressure, so that a pressurized system is preferred. The pressure varies depending upon the conditions such as the oxygen concentration in the gas. For example, in the case of air, the pressure is usually from 1 to 150 kg/cm².G, preferably from 10 to 100 kg/cm².G.

The oxidation treatment is carried out usually at a temperature of from 60 to 160° C., preferably from 80 to 150° C., more preferably from 100 to 140° C., in a state where the rhodium-containing liquid and the accelerator-containing aqueous medium are sufficiently stirred.

The system for the oxidation reaction is not particularly limited and may be a batch system or a continuous system. Further, an organic phase after extracting rhodium into an aqueous phase, followed by phase separation, may be again contacted with an aqueous medium containing the accelerator to repeat the oxidation treatment, and such a method is effective to improve the recovery of rhodium.

The mechanism for the recovery of rhodium in the treatment with an oxidizing agent is considered to be as follows, although its details are not clearly understood. Namely, from a rhodium species bonded to a complex-forming ligand present in the solution, the ligand is dissociated by the oxidation treatment, and the oxidized state of rhodium is increased, whereby its solubility in an aqueous phase is improved. At the time of this oxidation treatment, by the presence of an aqueous medium simultaneously in the system, the oxidized rhodium species more readily transfers to the aqueous phase, as compared with a case where only the organic phase is present, whereby the oxidation reaction is considered to proceed more efficiently.

Recovery of rhodium from a reaction solutions and regeneration and recycling of a catalyst (process for producing an aldehyde)

The process of the present invention is effectively applicable to a process for producing an aldehyde by hydroformylation of a compound having an olefinic unsaturated bond with carbon monoxide and hydrogen in a water-insoluble solvent in the presence of a rhodium complex.

Such a process for producing an aldehyde comprises the following steps:

1) a waste catalyst separation step of separating a rhodium-containing liquid from a hydroformylation reaction step, 2) an oxidation/extraction step of subjecting the rhodium-containing liquid to oxidation treatment in the presence of an aqueous medium containing a recovery accelerator to extract rhodium into an aqueous phase, 3) a rhodium-containing aqueous phase separation step of separating the aqueous phase from an organic phase, 4) a complexing step of contacting the aqueous phase containing rhodium, with an organic solvent solution of a water-insoluble tertiary organic phosphorus compound, in a gas atmosphere containing carbon monoxide, to extract rhodium in the form of a tertiary organic phosphorus compound complex into the organic solvent, 5) a rhodium complex separation step of separating the organic phase from the aqueous phase, and 6) a recycling step of recycling the organic phase containing the rhodium-tertiary organic phosphorus compound complex to the above-mentioned hydroformylation step.

The compound having an olefinic unsaturated bond to be used as a starting material in the hydroformylation reaction step, is not particularly limited, and it may for example, be a $C_{2-20}$ olefinic hydrocarbon such as ethylene, propylene, 1-butene, 2-butene, isobutene, a butene mixture, butene dimer, hexene, octene, nonene or propylene trimer, or a mixture thereof, or an olefinic compound having a functional group, such as allyl alcohol, vinyl acetate or vinyl chloride. Preferred is an olefinic hydrocarbon.

As the catalyst, a complex having rhodium combined with a complex-forming ligand, may be employed. The complex-forming ligand may be an organic phosphorus compound. Specifically, a tertiary alkyl or arylphosphine, or a tertiary alkyl or arylphosphite may be used. Specifically, it may, for example, be a trialkylphosphine such as trimethylphosphine, triethylphosphine, tripropylphosphine, tributylphosphine or trioctylphosphine, a triarylphosphine such as triphenylphosphine, tritoluylphosphine or trixylylphosphine, or a tertiary alkylarylphosphine such as diphenylpropylphosphine or phenyldipropylphosphine. The phosphite may, for example, be a phosphite having a low hydrolyzability due to a steric hindrance, such as triethylphosphite, triphenylphosphite or tris(o-tert-butylphenyl)phosphite. Further, a mixture of a phosphine and a phosphite may be employed. Preferred is a triarylphosphine, and particularly preferred is triphenylphosphine.

The hydroformylation reaction is carried out in a hydrocarbon solvent such as toluene or in a water-insoluble solvent such as a high boiling point byproduct formed by the hydroformylation reaction. After the reaction, the crude product is separated by a means such as distillation or stripping by an unreacted gas, and the catalyst may be retained in the reaction zone, or may be once withdrawn and then returned to the reaction zone and used for the reaction. In either method, in order to avoid accumulation of deactivated catalyst metals or by-products such as high boiling point substances, the waste catalyst solution containing the catalyst is withdrawn out of the reaction zone continuously or intermittently (the waste catalyst separation step).

In this rhodium-containing liquid separated from the hydroformylation step, rhodium is dissolved in a solution wherein the starting material, the reaction product, by-products and the solvent for reaction are mixed. The process of the present invention can be applied to a reaction solution containing a formed aldehyde. However, it is preferably applied to a catalyst solution having substantially all the aldehyde distilled off by distillation or stripping, or to a catalyst solution obtained by concentrating the solvent for reaction or the high boiling point by-products, or to a residual metal-containing liquid obtained by partially removing the ligand or the metal complex from these catalyst solutions. More preferably, it is applied to a solution having the ligand and the formed aldehyde removed.

The concentration of rhodium in such a rhodium-containing liquid is not particularly limited, but it is preferably from 10 to 10,000 ppm, more preferably from 50 to 1,000 ppm.

In the oxidation/extraction step, the above rhodium-containing liquid is subjected to oxidation treatment in the presence of an aqueous medium containing a recovery accelerator, and rhodium is extracted into the aqueous medium phase. The recovery accelerator to be used here is a water-soluble substance which accelerates the reaction for oxidation treatment of rhodium to extract it into the aqueous phase, and as mentioned above, it is preferably at least one member selected from the group consisting of (A) a $C_{2-8}$ carboxylic acid, preferably a $C_{2-4}$ carboxylic acid, more preferably an aliphatic monocarboxylic acid or dicarboxylic acid, particularly acetic acid, (B) an amine or an amine salt, preferably an aliphatic amine having a polar substituent or a heterocyclic amine, (C) ammonia or an ammonium salt, preferably an ammonium salt of an aliphatic carboxylic acid or an aromatic carboxylic acid, or an ammonium salt of an inorganic acid, and (D) an inorganic acid or an inorganic acid salt, preferably at least one acid selected from the group consisting of sulfuric acid, nitric acid, hydrochloric acid, carbonic acid, phosphoric acid and boric acid, and the alkali metal is sodium or potassium.

Then, the obtained rhodium-containing aqueous medium phase is separated from the organic phase (the rhodium-containing aqueous phase separation step). Then, this aqueous phase is contacted with an organic solvent solution of a water-insoluble tertiary organic phosphorus compound in a gas atmosphere containing carbon monoxide, to extract rhodium in the form of the tertiary organic phosphorus compound complex into the organic solvent (the complexing step).

The obtained organic phase containing the complex is separated from the aqueous phase (the rhodium complex separation step), and this organic phase is recycled to the above-mentioned hydroformylation reaction step (the recycling step).

Among these respective steps, the portions characteristic in the present invention are as described above with respect to the respective operations.

Now, the present invention will be described in further detail with reference to Examples. However, it should be understood that the present invention is by no means restricted by such specific Examples. In the following Examples, "%" means "wt %" unless otherwise specified.
Process for preparing a rhodium complex solution

EXAMPLE 1

100 ml of a rhodium aqueous solution (Rh concentration: 294.2 mg/l) prepared by diluting a commercially available rhodium sulfate aqueous solution (Rh concentration 11%) with water, and 100 ml of a toluene solution containing 25% of triphenylphosphine, were charged into a 0.5 l autoclave of up and down agitating type, and water gas ($H_2$:CO—1:1 (volume ratio), the same applies to the following Examples) was introduced at room temperature and pressurized to 20 kg/cm$^2$.G. Then, the temperature was raised to 130° C., followed by stirring treatment for 2 hours. After the treatment, the temperature was lowered to room temperature, the water gas was released, and the system was left to stand still. Then, the oil phase (the organic phase) and the aqueous phase were separated, and the rhodium concentrations in the respective phases were analyzed by a Zeeman atomic absorption method. From the results, the amount of rhodium transferred from the charged aqueous solution to the oil phase (the recovery) was obtained in accordance with the following formula (1) and found to be 99.6%.

$$\text{Recovery}(\%) = \left(1 - \frac{\text{Amount of } Rh \text{ in the aqueous phase}}{\text{Amount of } Rh \text{ in the charged aqueous solution}}\right) \times 100 \quad (1)$$

EXAMPLE 2

100 ml of a rhodium aqueous solution (Rh concentration: 355.9 mg/l) prepared by diluting a commercially available rhodium nitrate aqueous solution (Rh concentration: 5.1%) with water, and 100 ml of a toluene solution containing 25% of triphenylphosphine, were charged into a 0.5 lautoclave of up and down agitating type, and water gas was introduced at room temperature and pressurized to 20 kg/cm$^2$.G. Then, the temperature was raised to 130° C., followed by stirring treatment for 2 hours. After the treatment, the temperature was lowered to room temperature, the water gas was released, and the system was left to stand still. Then, the oil phase (the organic phase) and the aqueous phase were separated, and the rhodium concentrations in the respective phases were analyzed by a Zeeman atomic absorption method. As a result, the recovery of rhodium was 99.2%.

EXAMPLE 3

100 ml of a rhodium aqueous solution (Rh concentration: 265.5 mg/l) prepared by diluting rhodium chloride with water, and 100 ml of a toluene solution containing 25% of triphenylphosphine, were charged into a 0.5 l autoclave of up and down agitating type, and water gas was introduced at room temperature and pressurized to 20 kg/cm$^2$.G. Then, the temperature was raised to 130° C., followed by stirring treatment for 2 hours. After the treatments the temperature was lowered to room temperature, the water gas was released, and the system was left to stand still. Then, the oil phase (the organic phase) and the aqueous phase were separated, and the rhodium concentrations in the respective phases were analyzed by a Zeeman atomic absorption method. As a resultg the recovery of rhodium was 97.2%.

EXAMPLE 4

50 ml of a rhodium aqueous solution (Rh concentration: 577.4 mg/l) prepared by diluting a commercially available rhodium acetate aqueous solution (Rh concentration: 10%, containing a small amount of acetic acid) with water, and 50 ml of a toluene solution containing 25% of triphenylphosphine, were charged into a 0.5 l autoclave of up and down agitating type, and water gas was introduced at room temperature and pressurized to 20 kg/cm$^2$.G. Then, the temperature was raised to 130° C., followed by stirring treatment for 0.5 hour. After the treatment, the temperature was lowered to room temperature, the water gas was released, and the system was left to stand still. Then, the oil phase (the organic phase) and the aqueous phase were separated, and the rhodium concentrations in the respective phases were analyzed by a Zeeman atomic absorption method. As a result, the recovery of rhodium was 99.9%.

EXAMPLE 5

50 ml of a rhodium aqueous solution (Rh concentration: 489.7 mg/l, acetic acid concentration: 15.1%) prepared by diluting the same commercially available rhodium acetate aqueous solution as used in Example 4, with water and acetic acid, and 50 ml of a toluene solution containing 25% of triphenylphosphine, were charged into a 0.5 l autoclave of up and down agitating type, and water gas was introduced at room temperature and pressurized to 20 kg/cm$^2$.G. Then, the temperature was raised to 130° C., followed by stirring treatment for 0.5 hour. After the treatment, the temperature was lowered to room temperature, the water gas was released, and the system was left to stand still. Then, the oil phase (the organic phase) and the aqueous phase were separated, and the rhodium concentrations in the respective phases were analyzed by a Zeeman atomic absorption method. As a result, the recovery of rhodium was 99.8%.

EXAMPLE 6

A solution consisting mainly of hydroformylated high boiling point substances and triphenylphosphine, obtained by removing an unreacted starting material, the aldehyde product and the reaction solvent from a solution of a hydroformylation reaction of propylene using rhodium/triphenylphosphine as a catalyst, was subjected to oxidation treatment with air in the presence of water. Then, the aqueous phase was separated to obtain an aqueous solution containing a rhodium compound. 60 ml of this aqueous solution (Rh concentration: 146.9 mg/l) and 60 ml of a toluene solution containing 25% of triphenylphosphine were charged into a 0.5 l autoclave of up and down agitating type and subjected to stirring treatment at 130° C. for 0.5 hour in an atmosphere of 50 kg/cm$^2$.G of water gas. After the treatment, the temperature was lowered, the water gas was released, and the system was left to stand still, whereupon the aqueous phase and the organic phase (oil phase) were separated. The rhodium concentrations of the respective phases were analyzed by a Zeeman atomic absorption method. As a result, the recovery of rhodium was 92.3%.

EXAMPLE 7

The same solution consisting mainly of hydroformylated high boiling point substances and triphenylphosphine as used in Example 6, was subjected to oxidation treatment with air in the presence of water. Then, the aqueous phase was separated to obtain an aqueous solution containing a rhodium compound. 50 ml of a rhodium aqueous solution (Rh concentration: 116.5 mg/l, acetic acid concentration: 20%) prepared by adding acetic acid to this aqueous solution, was subjected to contacting treatment with 50 ml of a toluene solution containing 20% of triphenylphosphine in the same manner as in Example 6. As a result, the recovery of rhodium was 991%.

EXAMPLE 8

The same solution consisting mainly of hydroformylated high boiling point substances and triphenylphosphine as used in Example 6, was subjected to oxidation treatment with air in the presence of a 1M/l sulfuric acid aqueous solution. Then, the aqueous phase was separated to obtain a rhodium-containing aqueous solution (Rh concentration: 107.4 mg/l). 170 ml of this rhodium-containing aqueous solution and 50 ml of a toluene solution containing 25% of triphenylphosphine were charged into a 0.5 l autoclave of up and down agitating type and subjected to stirring treatment at 130° C. for 0.5 hour in an atmosphere of 50 kg/cm$^2$.G of water gas. After the treatment, the temperature was lowered, the water gas was released, and the system was left to stand still, whereupon the aqueous phase and the organic phase (the oil phase) were separated. The rhodium concentrations of the respective phases were analyzed by a Zeeman atomic absorption method. As a result, the recovery of rhodium was 74.9%.

EXAMPLE 9

The same solution consisting mainly of hydroformylated high boiling point substances and triphenylphosphine as used in Example 6, was subjected to oxidation treatment in the presence of a 0.1M/l monoethanolamine aqueous solution to obtain a rhodium aqueous solution (Rh concentration: 125.6 mg/l). Using 60 ml of this rhodium aqueous solution and 60 ml of a toluene solution containing 25% of triphenylphosphine, treatment was conducted under the same conditions as in Example 6, and the recovery of rhodium transferred to the oil phase was obtained. The recovery was 88.3%.

EXAMPLE 10

The same solution consisting mainly of hydroformylated high boiling point substances and triphenylphosphine as used in Example 6, was subjected to oxidation treatment with a 1M/l monoethanolamine aqueous solution to obtain an aqueous solution (Rh concentration: 245.5 mg/l). This aqueous solution was treated with a toluene solution containing 25% of triphenylphosphine in the same manner as in Example 6. As a result, the recovery of rhodium was 57.2%.

EXAMPLE 11

The same solution consisting mainly of hydroformylated high boiling point substances and triphenylphosphine as used in Example 6, was subjected to oxidation treatment with a 1M/l diethanolamine aqueous solution to obtain an aqueous solution (Rh concentration: 91.9 mg/l). This aqueous solution was treated with a toluene solution containing 25% of triphenylphosphine in the same manner as in Example 6. As a result, the recovery of rhodium was 48.1%.

EXAMPLE 12

The same solution consisting mainly of hydroformylated high boiling point substances and triphenylphosphine as used in Example 6, was subjected to oxidation treatment with a 1M/l methylethanolamine aqueous solution to obtain an aqueous solution (Rh concentration: 97.2 mg/l). This aqueous solution was treated with a toluene solution containing 25% of triphenylphosphine in the same manner as in Example 6. As a result, the recovery of rhodium was 41.1%.

EXAMPLE 13

The same solution consisting mainly of hydroformylated high boiling point substances and triphenylphosphine as used in Example 6, was subjected to oxidation treatment with a 1M/l ammonium acetate aqueous solution to obtain an aqueous solution (Rh concentration: 163.4 mg/l). This aqueous solution and a toluene solution containing 25% of triphenylphosphine were treated at 130° C. for 4 hours in an atmosphere of 50 kg/cm$^2$.G of water gas. As a result, the recovery of rhodium was 79.6%.

COMPARATIVE EXAMPLE 1

The same solution consisting mainly of hydroformylated high boiling point substances and triphenylphosphine as used in Example 13, was subjected to oxidation treatment with a 1M/l ammonium acetate aqueous solution to obtain an aqueous solution. This aqueous solution and a toluene solution containing 25% of triphenylphosphine were charged into a 0.5 l autoclave of up and down agitating type under nitrogen and treated at 130° C. for 6 hours. As a result, the recovery of rhodium was 8.7%.

EXAMPLE 14

Acetic acid was added to the same rhodium aqueous solution obtained by treatment with an ammonium acetate aqueous solution as in Example 13 to obtain an aqueous solution (Rh concentration: 218 mg/l, acetic acid concentration: 20%). This aqueous solution was treated at 150° C. for 0.5 hour in the same manner as in Example 13. As a result, the recovery of rhodium was 88.4%.

EXAMPLE 15

Acetic acid was added to the same rhodium aqueous solution obtained by treatment with an ammonium acetate aqueous solution as in Example 13 to obtain an aqueous solution (Rh concentration: 263.2 mg/l, acetic acid concentration: 20%). Using this aqueous solution and a toluene solution containing 25% of triphenylphosphine, treatment was carried out in the same manner as in Example 13. As a result, the recovery of rhodium was 87.4%.

EXAMPLE 16

The same reaction solution consisting mainly of hydroformylated high boiling point substances and triphenylphosphine as in Example 6, was subjected to oxidation treatment in the presence of a 20% acetic acid aqueous solution to obtain a rhodium-containing aqueous solution. 50 ml of this aqueous solution (Rh concentration: 239.0 mg/l, acetic acid concentration: about 14 to 15%) and 50 ml of a toluene solution containing 25% of triphenylphosphine were charged into a 0.5 l autoclave of up and down agitating type and subjected to stirring treatment at 130° C. for 0.5 hour in an atmosphere of 20 kg/cm$^2$.G of water gas. As a result, the recovery of rhodium was 99.9%.

EXAMPLE 17

75 ml of a rhodium-containing aqueous solution (Rh concentration: 117.4 mg/l) obtained in the same manner as in Example 16 and 25 ml of a toluene solution containing 25% of triphenylphosphine were charged into a 0.5 l autoclave of up and down agitating type and subjected to stirring treatment at 130° C. for 0.5 hour in an atmosphere of 20 kg/cm$^2$.G of water gas. After the treatment, the temperature was lowered, the water gas was released, and the system was left to stand still, whereupon the oil phase and the aqueous phase were separated. The rhodium concentrations of the respective phases were analyzed by a Zeeman atomic absorption method. As a result, the recovery was 99.9%.

EXAMPLE 18

150 ml of a rhodium-containing aqueous solution (Rh concentration 110.2 mg/l) obtained in the same manner as in Example 16 and 50 ml of a toluene solution containing 25% of triphenylphosphine were charged into a 0.5 l autoclave of induction rotation stirring type and subjected to stirring treatment at 130° C. for 2 hours at a rotational speed of 750 rpm in an atmosphere of 18 kg/cm$^2$.G of water gas. After the treatment, the temperature was lowered, the water gas was released, and the system was left to stand still, whereupon the oil phase and the aqueous phase were separated. The rhodium concentrations of the respective phases were analyzed by a Zeeman atomic absorption method. As a result, the recovery was 99.6%.

EXAMPLES 19 to 23

Experiments were carried out in the same manner as in Example 16 except that the treating temperature, the time, the rotational speed and the concentration of triphenylphosphine (TPP) were changed. The results are shown in the following Table 1.

TABLE 1

| Example No. | Rh concentration (mg/l) | Temp. (° C.) | Time (hr) | Rotational speed (rpm) | TPP concentration (%) | Recovery (%) |
|---|---|---|---|---|---|---|
| 19 | 110.2 | 130 | 2 | 500 | 25 | 99.5 |
| 20 | 134.1 | 120 | 2 | 500 | 25 | 99.3 |
| 21 | 134.1 | 120 | 4 | 1,000 | 25 | 99.6 |
| 22 | 99.4 | 120 | 2 | 1,000 | 10 | 99.2 |
| 23 | 89.0 | 120 | 2 | 1,000 | 5 | 99.1 |

EXAMPLE 24

50 ml of a rhodium-containing aqueous solution (Rh concentration: 192.0 mg/l) obtained in the same manner as in Example 16 and 50 ml of a mixed octene solution containing 0.59% of triphenylphosphine were charged into a 0.5 l autoclave of up and down agitating type and subjected to stirring treatment at 130° C. for 0.5 hour in a atmosphere of 50 kg/cm$^2$.G of water gas. After the treatment, the temperature was lowered, the water gas was released, and the system was left to stand still, whereupon the oil phase and the aqueous phase were separated. The rhodium concentrations of the respective phases were analyzed by a Zeeman atomic absorption method. As a result the recovery was 99.6%.

EXAMPLES 25 and 26

Experiments were carried out in the same manner as in Example 24 except that the oil/water ratio and the concentration of triphenylphosphine were changed. The results are shown in the following Table 2.

TABLE 2

| Example No. | Rh concentration (mg/l) | Oil/water (volume ratio) | TPP concentration (%) | Reaction pressure (kg/cm$^2$ · G) | Recovery (%) |
|---|---|---|---|---|---|
| 25 | 206.0 | 2 | 0.59 | 50 | 98.5 |
| 26 | 237.9 | 2 | 3.03 | 20 | 99.0 |

Recovery of rhodium from a hydroformylation reaction solution (Recovery accelerator=carboxylic acid)

A catalyst solution having the composition as identified in the following Table 3, which was obtained by removing unreacted propylene, the aldehyde product and the reaction solvent from a solution of a hydroformylation reaction of propylene using a rhodium/triphenylphosphine type complex as a catalyst, was used as a starting material for recovery, and the following experiments were carried out. Further, a gas chromatography analysis of the starting material for recovery was carried out, whereby the results were as shown in Table 40.

TABLE 3

| | |
|---|---|
| Rhodium | 350 mg/l |
| Triphenylphosphine | 10% |
| Triphenylphosphine oxide | 2% |

TABLE 4

| Retention time (min) | Weight (%) |
|---|---|
| 10 to 16.5 | 30.0 |
| 16.5 to 21 | 48.4 |
| 21 to | 9.3 |

Conditions for gas chromatography

Column: UA 1HT 0.25 mm×17 m

Carrier gas: He 1.5 ml/min

Split: 1/80

Temperature rise: Maintained at 50° C. for 5 minutes→temperature rise (10° C./min)→maintained at 390° C. for 7 minutes Inlet temperature: 400° C.

Detector temp/type: 420° C., FID

EXAMPLE 27

50 ml of the above-mentioned starting material for recovery and 50 ml of a 40 wt % acetic acid aqueous solution were charged into a 500 ml stainless steel autoclave of induction stirring type, and air was introduced and pressurized to 100 kg/cm$^2$.G, followed by treatment at 120° C. for 2 hours at a rotational speed of 1000 rpm. The temperature was lowered to room temperatures the air was released and the system was left to stand still, whereupon the oil phase and the aqueous phase were separated, and the aqueous phase was recovered. The analysis of rhodium was carried out by a Zeeman atomic absorption method. As a results the extraction ratio of rhodium was 79.9%. Here, the extraction ratio of rhodium was calculated by the following formula (2).

Extraction ratio of rhodium=(Amount of Rh extracted into the aqueous phase/amount of Rh in the starting material)×100 (2)

EXAMPLE 28

The recovery and extraction of rhodium were carried out in the same manner as in Example 27 except that the concentration of the acetic acid aqueous solution used was changed to 20 wt %. The results are shown in Table 5 together with the results of Example 27.

TABLE 5

| Example No. | Acetic acid concentration (wt %) | Extraction ratio (%) |
| --- | --- | --- |
| 27 | 40 | 79.9 |
| 28 | 20 | 74.3 |

EXAMPLES 29 and 30

The recovery and extraction of rhodium were carried out in the same manner as in Example 27 except that acetic acid used was changed to the carboxylic acid as identified in Table 6. The results are shown in Table 60.

TABLE 6

| Example No. | Carboxylic acid | Extraction ratio (%) |
| --- | --- | --- |
| 29 | Oxalic acid | 84.9 |
| 30 | Malic acid | 86.0 |

EXAMPLE 31

50 ml of the above-mentioned starting material for recovery and 50 ml of a 20 wt % acetic acid aqueous solution were charged into a 500 ml stainless steel autoclave of induction stirring type, and air was introduced and pressurized to 20 kg/cm$^2$.G. While supplying air at a flow rate of 40 Nl/hr, treatment was carried out at 120° C. for 2 hours at a rotational speed of 1,000 rpm. Then, feeding of the gas was stopped, and the temperature was lowered to room temperature. Then, air was released and the system was left to stand still, whereupon the oil phase and the aqueous phase were separated, and the aqueous phase was recovered. As a result, the recovery of rhodium was 65.3%.

EXAMPLES 32 to 42

The recovery of rhodium was carried out in the same manner as in Example 31 except that the reaction conditions were changed as identified in the following Table 7. The reaction conditions and the results are shown in Table 7.

stirring type, and air was supplied and pressurized to 20 kg/cm$^2$.G. While supplying air in a gas flow rate of 40 Nl/hr, treatment was carried out at 120° C. for 2 hours at a rotational speed of 1,000 rpm. Then, feeding of the gas was stopped, and the temperature was lowered to room temperature, then the air was released and the system was left to stand still, whereupon the oil phase and the aqueous phase were separated, and the aqueous phase was recovered. As a result, the extraction ratio of rhodium into the aqueous phase was 64.1%.

The residual organic phase after the above treatment was used as a starting material for recovery and treated in the same manner as above. As a result, the extraction ratio of rhodium into the aqueous phase for the second time was 58.7%. Further, the overall extraction ratio up to the second time was 85.2%. Further, the oil phase of the second time was used as a starting material for recovery, and again treated in the same manner as above. As a result, the extraction ratio of rhodium into the aqueous phase for the third time was 50.1%. The overall extraction ratio up to the third time was 93.0%.

EXAMPLE 44

A rhodium-containing liquid consisting mainly of high boiling point by-products, which was obtained by removing an unreacted starting material and the aldehyde product from a solution of a hydroformylation reaction of an octene mixture using a rhodium/triphenylphosphine oxide type complex as a catalyst, was used as a starting material for recovery, and the following experiment was carried out. The amount of rhodium contained in this starting material for recovery was 100 mg/l.

50 ml of the starting material for recovery and 50 ml of a 20 wt % acetic acid aqueous solution were charged into a 500 ml stainless steel autoclave of induction stirring type, and air was supplied and pressurized to 100 kg/cm$^2$.G, followed by treatment at 120° C. for 2 hours at a rotational speed of 1,000 rpm. The temperature was lowered to room temperature, then the air was released, and the system was left to stands till, whereupon the oil phase and the aqueous phase were separated, and the aqueous phase was recovered. As a result, the extraction ratio of rhodium was 97.9%.

COMPARATIVE EXAMPLE 2

Into a 500 ml stainless steel autoclave of up and down agitating type, 75 g of the starting material for recovery, 225

TABLE 7

| Example No. | Acetic acid (wt %) | Temp. (° C.) | Pressure (kg/cm$^2$ · G) | Time (hr) | Gas flow rate (Nl/h) | Polar solvent/ catalyst solution | Extraction ratio (%) |
| --- | --- | --- | --- | --- | --- | --- | --- |
| 32 | 10 | 120 | 20 | 2 | 40 | 1/1 | 54.3 |
| 33 | 20 | 120 | 20 | 2 | 40 | 1/1 | 65.3 |
| 34 | 20 | 140 | 20 | 2 | 40 | 1/1 | 54.8 |
| 35 | 40 | 140 | 50 | 2 | 40 | 1/1 | 62.1 |
| 36 | 20 | 120 | 20 | 2 | 5 | 1/1 | 62.6 |
| 37 | 10 | 120 | 10 | 2 | 40 | 1/1 | 50.0 |
| 38 | 20 | 140 | 50 | 2 | 40 | 1/1 | 62.2 |
| 39 | 10 | 140 | 20 | 2 | 40 | 1/1 | 61.7 |
| 40 | 20 | 100 | 20 | 6 | 40 | 1/1 | 52.7 |
| 41 | 20 | 100 | 20 | 27 | 40 | 1/1 | 53.1 |
| 42 | 10 | 120 | 20 | 2 | 40 | 4/1 | 71.5 |

EXAMPLE 43

50 ml of the above-mentioned starting material for recovery and 50 ml of a 20 wt % acetic acid aqueous solution were charged into a 500 ml stainless steel autoclave of induction g of xylene, 3.1 g of 30% sodium hydroxide and 2.7 g of acetic acid were charged and heated to 78° C. in 15 minutes with stirring. Then, air was introduced through an immersed tube at a rate of 120 Nl/hr under a pressure of 2 MPa over a period of 21 hours. The reaction was carried out at a constant internal pressure of 2 MPa at a constant temperature of 80° C. The waste gas was released via a needle valve at the autoclave cover and sent to a cooled trap. After completion of the reaction, the content of the autoclave was cooled to 60° C. over a period of about 15 minutes, and supply of air was terminated. Then, 100 g of water was added to the reaction mixture, followed by stirring for 15 minutes at 60° C. The treated liquid was taken out from the reactor and subjected to phase separations. The organic phase was further extracted twice each time with 50 g of water. After all the treatments, the organic phase contained 15.5 mg of rhodium which corresponded to 60% of rhodium contained in the starting material. Thus, the extraction ratio of rhodium into the aqueous phase was 40%.

(Recovery accelerator=an amine an amine salt)

As a catalyst solution obtained by removing an unreacted propylene, the aldehyde product and the reaction solvent from a solution of a hydroformylation reaction of propylene using a rhodium/triphenylphosphine type complex as a catalyst, to be used as a starting material for recovery, the same one as used in the above-described experiment wherein a carboxylic acid was used as the recovery accelerator, was used, and the following experiments were carried out.

EXAMPLE 45

50ml of the above starting material for recovery and 50 ml of a 1 mol/l monoethanolamine aqueous solution were charged into a 500 ml stainless steel autoclave of up and down agitating type, and air was introduced and pressurized to 100 kg/cm$^2$.G, followed by treatment at 120° C. for 6 hours. The temperature was lowered to room temperature, then the air was released, and the system was left to stand still, whereupon the oil phase and the aqueous phase were separated, and the aqueous phase was recovered. The oil phase was further washed twice with water, and the washing water was recovered by combining it with the previous aqueous phase. The analysis of rhodium was carried out by a Zeeman atomic absorption method. As a result, the extraction ratio of rhodium was 94.5%. The extraction ratio of rhodium was calculated by the formula (2) in the same manner as described above.

EXAMPLES 46 to 49

Experiments were carried out in the same manner as in Example 45 except that the monoethanolamine aqueous solution used was changed to the following amines. The results are shown in the following Table (Table 8).

TABLE 8

| Example No. | Amine | Extraction ratio (%) |
| --- | --- | --- |
| 46 | Methylethanolamine, | 95.7 |
| 47 | Diethanolamine | 95.9 |
| 48 | Tetramethylethylenediamine | 80.4 |
| 49 | Pyridine | 79.2 |

EXAMPLE 50

The extraction experiment was carried out in the same manner as in Example 45 except that a solution prepared by adding 3 g (0.05 mol) of acetic acid to 50 ml (0.05 mol) of a 1 mol/l monoethanolamine aqueous solution, and 50 ml of the rhodium-containing liquid as the above starting material for recovery, were charged into the autoclave.

The extraction ratio of rhodium was 95%.

EXAMPLE 51

In the same manner as in Example 45, after contacting with the monoethanolamine aqueous solution and air, the residual oil phase separated from the aqueous phase containing rhodium, was again contacted with a 1 mol/l monoethanolamine aqueous solution and air for oxidation and extraction. As a result, the extraction ratio by the second treatment was 80%. The overall extraction ratio against the rhodium-containing liquid was 98.9%.

COMPARATIVE EXAMPLE 3

Treatment was carried out in the same manner as in Example 45 except that the amine or amine salt aqueous solution was changed to pure water. The extraction ratio of rhodium was 68.9%.

COMPARATIVE EXAMPLE 4

The process disclosed in JP-A-3-146423 was carried out by using the same rhodium-containing liquid as used in the above Example 45. Into a 500 ml stainless steel autoclave of up and down agitating type, 75 g of the rhodium-containing liquid, 225 g of xylene, 3.1 g of a 30% sodium hydroxide aqueous solution and 2.7 g of acetic acid were charged and heated to 78° C. in 15 minutes with stirring. Then, air was supplied through an immersed tube at a rate of 120 l/hr under a pressure of 2 MPa for 21 hours. The reaction was carried out at a constant internal pressure of 2 MPa at a constant temperature of 80° C. The waste gas was released via a needle valve at the autoclave cover and sent to a cooled trap. After completion of the reaction, the content of the autoclave was cooled to 60° C. over a period of about 15 minutes, and supply of air was terminated. 100 g of water was added to the reaction mixtures followed by stirring further for 15 minutes at 60° C. The treated liquid was taken out from the reactor and subjected to phase separation. The organic phase was further extracted twice each time with 50 g of water. After all the treatments, the organic phase contained 15.5 mg of rhodium which corresponded to 60% of rhodium contained in the starting material (the extraction ratio into the aqueous phase: 40%).

(Recovery accelerator=ammonia, an ammonium salt)

As the starting material for recovery, the same one as used in the above experiment wherein a carboxylic acid or an amine was used as the recovery accelerator, was used, and the following experiments were carried out.

EXAMPLE 52

50ml of the above starting material for recovery as a rhodium-containing liquid and 50 ml of a 2 mol/l ammonium acetate aqueous solution were charged into a 500 ml stainless steel autoclave of up and down agitating type, and air was supplied and pressurized to 100 kg/cm$^2$.G, followed by treatment at 120° C. for 6 hours. The temperature was lowered to room temperature, then the air was released, and the system was left to stand still, whereupon the oil phase and the aqueous phase were separated, and the aqueous phase was recovered. The oil phase was further washed twice with an equal amount of water, and the washing water was recovered by combining it with the previous aqueous phase. The analysis of rhodium was carried out by a Zeeman atomic absorption method. As a result, the extraction ratio of rhodium was 92.8%. Here, the extraction ratio of rhodium was calculated by the formula (2) in the same manner as described above.

EXAMPLES 53 and 54

Treatment was carried out in the same manner as in Example 52 except that the concentration of the ammonium acetate aqueous solution was changed. The results are shown in Table 9 together with the data of Example 52.

TABLE 9

| Example No. | Concentration of ammonium acetate | Extraction ratio (%) |
|---|---|---|
| 52 | 2mol/l | 92.8 |
| 53 | 1mol/l | 91.1 |
| 54 | 0.5mol/l | 85.8 |

EXAMPLES 55 to 58

Experiments were carried out in the same manner as in the above Example 52 except that the ammonium acetate aqueous solution used, was changed to the following ammonia or ammonium salt. The results are shown in the following Table (Table 10).

TABLE 10

| Example No. | Ammonia/ammonium salt | Concentration (mol/l) | Extraction ratio (%) |
|---|---|---|---|
| 55 | Ammonia | 3 | 91.5 |
| 56 | Ammonia | 1 | 86.4 |
| 57 | Ammonium hydrogencarbonate | 1 | 85.4 |
| 58 | Ammonium sulfate | 1 | 72.1 |

EXAMPLE 59

A solution prepared by adding 0.37 g (0.05 mol) of propionic acid to 50 ml (0.05 mol) of 1 mol/l aqueous ammonia, and 50 ml of the rhodium-containing liquid as the above-mentioned starting material for recovery, were charged into the autoclave and the extraction experiment was carried out in the same manner as in Example 52. The recovery of rhodium was 89.6%.

EXAMPLES 60 and 61

50 ml of the above rhodium-containing liquid and the following volume of a 1 mol/l ammonium acetate aqueous solution were charged into the autoclave, and the extraction treatment was carried out in the same manner as in Example 52. The results are shown in Table 11.

TABLE 11

| Example No. | Amount of the ammonium acetate aqueous solution | Extraction ratio (%) |
|---|---|---|
| 60 | 5ml | 77.5 |
| 61 | 100ml | 92.6 |

EXAMPLE 62

50 ml of the oil phase remaining after extracting 91.1% of rhodium into the aqueous phase with a 1 mol/l ammonium acetate aqueous solution in accordance with Example 53, and 50 ml of a fresh 1 mol/l ammonium acetate aqueous solution were charged into the autoclave and second treatment was carried out at 120° C. for 6 hours under an air pressure of 100 kg/cm$^2$.G. The extraction ratio by the second treatment was 53.4%. The overall extraction ratio combined with the first treatment was 96.0%.

EXAMPLE 63

50 ml of the above-mentioned rhodium-containing liquid (the starting material for recovery) and 50 ml of a 1 mol/l ammonium acetate aqueous solution were charged into a 500 ml stainless steel autoclave of induction stirring types and air was supplied and pressurized to 100 kg/cm$^2$.G. While supplying air at a gas flow rate of 20 Nl/hr, treatment was carried out at 120° C. for 2 hours at a rotational speed of 1,000 rpm. Then, feeding of the gas was stopped and the temperature was lowered to room temperatures. Then, the air was released, and the system was left to stand still, whereupon the oil phase and the aqueous phase were separated, and the aqueous phase was recovered. The oil phase was further washed twice with an equal amount of water, and the washing water was recovered by combining it with the previous aqueous phase. The extraction ratio of rhodium obtained in the same manner as in Example 52, was 82.7%.

EXAMPLES 64 to 69

Recovery of rhodium was carried out in the same manner as in Example 63 except that the reaction conditions were changed as identified in the following Table 12. The reaction conditions and the results are shown in Table 12.

COMPARATIVE EXAMPLE 5

Treatment was carried out in the same manner as in the above Example 52 except that the ammonium acetate aqueous solution used was changed to pure water. As a result, the extraction ratio was 68.9%

TABLE 12

| Example No. | Temp. (° C.) | Pressure (kg/cm$^2$ · G) | Time (hr) | Gas flow rate (Nl/h) | Water/oil (vol/vol) | Extraction ratio (%) |
|---|---|---|---|---|---|---|
| 63 | 120 | 100 | 2 | 20 | 1/1 | 82.7 |
| 64 | 120 | 100 | 2 | 40 | 1/1 | 80.7 |
| 65 | 120 | 20 | 2 | 40 | 1/1 | 77.2 |
| 66 | 120 | 10 | 2 | 40 | 1/1 | 75.4 |
| 67 | 140 | 100 | 2 | 40 | 1/1 | 93.7 |
| 68 | 120 | 100 | 6 | 40 | 1/1 | 90.2 |
| 69 | 120 | 100 | 2 | 40 | 4/1 | 89.2 |

(Recovery accelerator=an alkali metal salt of an inorganic acid)

As the starting material for recovery, the same one as used in the above experiment wherein a carboxylic acid, an amine, ammonia or the like was used as the recovery accelerator, was used, and the following experiments were carried out.

EXAMPLE 70

50 ml of the above-mentioned starting material for recovery as a rhodium-containing liquid and 50 ml of a 1 mol/l sodium sulfate aqueous solution were charged into a stainless steel autoclave of up and down agitating type, and air was introduced and pressurized to 100 kg/cm$^2$.G, followed by treatment at 120° C. for 6 hours. The temperature was lowered to room temperatures then the air was released, and the system was left to stand still, whereupon the oil phase and the aqueous phase were separated, and the aqueous phase was recovered. The oil phase was further washed twice with an equal amount of water, and the washing water was recovered by combining it with the previous aqueous phase. The analysis of rhodium was carried out by a Zeeman atomic absorption method. As a result, the extraction ratio of rhodium was 87.0%. Here, the extraction ratio of rhodium was calculated by the formula (2) in the same manner as described above.

EXAMPLES 71 to 73

Treatment was carried out in the same manner as in Example 70 except that instead of the sodium sulfate aqueous solution, the following alkali metal salt of an inorganic acid was used. The results are shown in Table 13.

TABLE 13

| Example No. | Alkali metal salt of an inorganic acid | Extraction ratio (%) |
| --- | --- | --- |
| 71 | Disodium monohydrogen phosphate | 81.2 |
| 72 | Sodium chloride | 87.5 |
| 73 | Sodium borofluoride | 76.2 |

Recovery of rhodium from a reaction solutions and regeneration and recycling of a catalyst

EXAMPLE 74

Unreacted starting materials, the aldehyde product and the solvent for reaction, etc. were removed from a reaction solution of hydroformylation of propylene using a rhodium/triphenylphosphine as a catalyst, to obtain a rhodium-containing liquid (a waste catalyst solution) having the composition as identified in Table 14, consisting mainly of high boiling point by-products and triphenylphosphine. The composition of this rhodium-containing liquid as determined by the gas chromatography (GC) analysis was as shown in Table 15.

TABLE 14

| Rhodium | 279.1 mg/l |
| --- | --- |
| Triphenylphosphine | 10% |
| Triphenylphosphine oxide | 2% |

| Retention time (min) | Weight (%) |
| --- | --- |
| 10 to 16.5 | 30.3 |
| 16.5 to 21 | 48.4 |
| 21 to | 9.3 |

(Conditions for gas chromatography)

Column: UA 1HT 0.25 mm×17 m

Carrier gas: He 1.5 ml/min

Split: 1/80

Temperature rise: Maintained at 50° C. for 5 minutes→temperature rise (10C/min)→maintained at 390° C. for 7 minutes Inlet temperature: 400° C.

Detector temp/type: 420° C., FID 50 ml of this waste catalyst solution and 50 ml of an acetic acid aqueous solution were charged into a 0.5 l stainless steel autoclave of induction stirring types and air was supplied and pressurized to 100 kg/cm$^2$.G, followed by treatment at 120° C. for 2 hours at a rotational speed of 1,000 rpm. Then, the temperature was lowered to room temperature, then the air was released, and the system was left to stand still, whereupon the aqueous phase was separated. Further, the oil phase was washed with water, and the washing water was mixed with the extracted aqueous phase. As a result, the extraction ratio of rhodium into the aqueous phase was 74.9%.

This rhodium-containing aqueous phase was concentrated under reduced pressure by evaporation of water to obtain an aqueous solution having a Rh concentration of 127.8 mg/l 60 ml of this aqueous solution and 60 ml of a toluene solution containing 25% of triphenylphosphine (TPP) (oil/water ratio: 1/1) were charged into a 0.5 l autoclave of up and down agitating type, and water gas was supplied and pressurized to 50 kg/cm$^2$.G, followed by stirring at 130° C. for 0.5 hour. After the treatment, the temperature was lowered, and the system was left to stand still, whereupon the oil phase and the aqueous phase were separated. The rhodium concentrations of the obtained respective phases were analyzed by a Zeeman atomic absorption method, and the recovery against rhodium in the charged aqueous phase was calculated in accordance with the following formula (3), based on the amount of Rh remaining in the aqueous phase after the treatment, whereby the recovery of Rh was 99.6%.

$$\text{Recovery}(\%) = \left(1 - \frac{\text{Amount of } Rh \text{ in the aqueous phase after treatment}}{\text{Amount of } Rh \text{ in the charged aqueous phase}}\right) \times 100 \quad (3)$$

Accordingly, the overall recovery of rhodium from the initial waste catalyst solution from hydroformylation of propylene to the toluene solution, was 74.7%.

Using the toluene solution thus obtained, a hydroformylation reaction of propylene was carried out. Into an autoclave of up and down agitating type, 50 ml of this solution and 10 g of propylene were charged, and the reaction was carried out at 103° C. for 2.5 hours under a water gas pressure of 50 kg/cm$^2$.G. As a result, the conversion of propylene was 97.0%.

EXAMPLE 75

60 ml of the same waste catalyst solution (Rh concentration: 279.1 mg/l) as used in Example 74 and 60 ml of a 40% acetic acid aqueous solution were charged into a 0.5 l stainless steel autoclave of induction stirring type, and air was supplied and pressurized to 100 kg/cm$^2$.G, followed by treatment at 120° C. for 2 hours at a rotational speed of 1,000 rpm. Then, the temperature was lowered to room temperature, then the air was released, and the system was left to stand still, whereupon the aqueous phase was separated by phase separation. Further, the oil phase was washed with water, and the washing liquid was mixed with the extracted aqueous phase. As a result, the extraction ratio of rhodium into the aqueous phase was 79.9%. This aqueous solution was concentrated under reduced pressure by evaporating water to obtain an aqueous solution having a Rh concentration of 179.7 mg/l. 60 ml of this aqueous solution and 60 ml of a toluene solution containing 25% of TPP (oil/water ratio: 1/1) were charged into a 0.5 l autoclave of up and down agitating type. Then, water gas was supplied and pressurized to 50 kg/cm$^2$.G, followed by stirring at 130° C. for 0.5 hour. After the treatment, the temperature was lowered, and the system was left to stand still, whereupon the oil phase and the aqueous phase were separated. The rhodium concentrations of the respective phases were analyzed by a Zeeman atomic absorption method, and the recovery of Rh was determined in the same manner as in Example 74, whereby the recovery of Rh was 99.7%.

Accordingly, the overall recovery of rhodium from the initial waste catalyst solution from hydroformylation of propylene to the toluene solution, was 79.7%.

Using this toluene solution, a hydroformylation reaction of propylene was carried out. Into an autoclave of up and down agitating type, 50 ml of this solution and 10 g of propylene were charged, and the reaction was carried out at 96° C. for 3.5 hours under a water gas pressure of 50 kg/cm$^2$.G. As a result, the conversion of propylene was 95.2%.

EXAMPLE 76

60 ml of the same waste catalyst solution (Rh concentration 279.1 mg/l) as used in Example 74 and 60 me of a 20% acetic acid aqueous solution were charged into a 0.5 l stainless steel autoclave of induction stirring type, and air was supplied and pressurized to 100 kg/cm$^2$.G, followed by treatment at 120° C. for 2 hours at a rotational speed of 1,000 rpm. Then, the temperature was lowered to room temperature, then the air was released, and the system was left to stand still, whereupon the oil phase and the aqueous phase were separated, and the aqueous phase was recovered. Further, the oil phase was washed with water, and the washing liquid was mixed with the extracted aqueous phases. As a result, the extraction ratio of rhodium into the aqueous phase was 74.3%. The oil phase after treatment was used again as a starting material for recovery, and subjected to the same treatment as above.

As a result, the extraction ratio of rhodium into the aqueous phase for the second time was 61.2%. Further, the oil phase of the second time was used again as a starting material for recovery, and subjected to the same treatment as above. As a result, the extraction ratio of rhodium into the aqueous phase for the third time was 44.6%. The overall extraction ratio of rhodium into the aqueous phase up to the third time was 95%. The aqueous solution obtained by putting these extracted solutions of three times together, was concentrated under reduced pressure by evaporating water to obtain an aqueous solution having a Rh concentration of 158.7 mg/l.

60 ml of this aqueous solution and 60 ml of a toluene solution containing 25% of TPP (oil/water ratio: 1/1) were charged into a 0.5 l autoclave of up and down agitating type, and water gas was supplied and pressurized to 50 kg/cm$^2$.G, followed by stirring at 130° C. for 0.5 hour. After the treatment, the temperature was lowered, and the system was left to stand still, whereupon the oil phase and the aqueous phase were separated. The rhodium concentrations of the respective phases were analyzed by a Zeeman atomic absorption method, and the recovery of Rh was determined in the same manner as in Example 74. As a result, the recovery of Rh was 98.3%. Accordingly, the overall recovery of rhodium from the initial waste catalyst solution from hydroformylation of propylene to the toluene solution was 93.4%.

Using this toluene solution, a hydroformylation reaction of propylene was carried out. Into an autoclave of up and down agitating type, 50 ml of this solution and 10 g of propylene were charged, and the reaction was carried out at 96° C. for 4 hours under a water gas pressure of 50 kg/cm$^2$.G. As a result, the conversion of propylene was 951%.

EXAMPLE 77

100 ml of a waste catalyst solution (Rh concentration: 345.6 mg/l) from hydroformylation of propylene having the same composition as in Example 74 and 100 ml of a 20% acetic acid aqueous solution were charged into a 0.5 l stainless steel autoclave of induction stirring type, and air was supplied and pressurized to 20 kg/cm$^2$.G. While supplying air at a gas flow rate of 40 Nl/hr, treatment was carried out at 120° C. for 2 hours at a rotational speed of 1,000 rpm. Then, feeding of the gas was stopped, the temperature was lowered to room temperatures then the air was released, and the system was left to stand still, whereupon the oil phase and the aqueous phase were separated, and the aqueous phase was recovered.

As a result, the extraction ratio of rhodium into the aqueous phase was 64%. The oil phase after treatment was used again as a starting material for recovery and subjected to the same treatment as above.

As a result, the extraction ratio of the rhodium into the aqueous phase for the second time was 58.7%. The overall extraction ratio up to the second time was 85.2%. The oil phase of the second time was used again as a starting material for recovery and subjected to the same treatment as above. As a result, the extraction ratio of rhodium into the aqueous phase for the third time was 501%. The overall extraction ratio of rhodium into the aqueous phase up to the third time, was 93.0%. 180 ml of this aqueous solution (Rh concentration: 113.9 mg/l) obtained by putting these extracted solutions of three times together, and 60 ml of a toluene solution containing 25% of TPP (oil/water ratio: 3/1) were charged into a 0.5 e autoclave of induction rotational stirring type, and stirred at 130° C. for 0.5 hours at a rotational speed of 1,000 rpm under a water gas pressure of 20 kg/cm$^2$.G. After the treatment, the temperature was lowered, and the system was left to stand still, whereupon the oil phase and the aqueous phase were separated. The rhodium concentrations of the respective phases were analyzed by a Zeeman atomic absorption method, and the recovery of Rh was calculated in the same manner as in Example 74.

As a result, the recovery of Rh was 99.52%. Accordingly, the overall recovery of rhodium from the initial waste catalyst solution from hydroformylation of propylene to the toluene solution, was 92.6%.

Using this toluene solution, a hydroformylation reaction of propylene was carried out. Into an autoclave of up and down agitating type, 50 ml of this solution and 10 g of propylene were charged, and the reaction was carried out at 107° C. for 2.5 hours under a water gas pressure of 50 kg/cm$^2$.G. As a result, the conversion of propylene was 99.7%.

EXAMPLE 78

150 mg of the same waste catalyst solution (Rh concentration: 279.1 mg/l) as used in Example 74, and 150 ml of a 0.1M/l monoethanolamine aqueous solution were charged into a 0.5 l stainless steel autoclave of induction stirring types and air was supplied and pressurized to 100 kg/cm$^2$.G, followed by treatment at 120° C. for 6 hours at a rotational speed of 1,000 rpm. Then, the temperature was lowered to room temperature, then the air was released, and the system was left to stand still, whereupon the aqueous phase was separated. Further, the oil phase was washed with water, and the washing liquid was mixed with the extracted aqueous phase. As a result, the extraction ratio of rhodium into the aqueous phase was 58.9%. This aqueous phase was concentrated under reduced pressure by evaporating water to obtain an aqueous solution having a Rh concentration of 125.6 mg/l. 60 ml of this aqueous solution and 60 ml of a toluene solution containing 25% of TPP (oil/water ratio: 1/1) were charged into a 0.5 l autoclave of up and down agitating type, and stirred at 130° C. for 0.5 hour under a water gas pressure of 50 kg/cm$^2$.G. After the treatment, the temperature was lowered, and the system was left to stand still, whereupon the oil phase and the aqueous phase were separated. The rhodium concentrations of the respective phases were analyzed by a Zeeman atomic absorption method, and the recovery was obtained in accordance with the following formula (4), based on the amount of Rh extracted into the toluene phase after treatment, against rhodium in the charged aqueous phase.

Recovery (%)=(Amount of Rh extracted into the toluene phase/ amount of Rh in the charged aqueous phase)×100    (4)

As a result, the recovery of Rh was 88.3%. Accordingly, the overall recovery of rhodium from the initial waste catalyst solution from hydroformylation of propylene to the toluene solution was 52.0%.

Using this toluene solution, a hydroformylation reaction of propylene was carried out. Into an autoclave of up and down agitating type, 50 ml of this solution and 10 g of propylene were charged, and the reaction was carried out at 97° C. for 4 hours under a water gas pressure of 50 kg/cm$^2$.G. As a result, the conversion of propylene was 92.6%.

EXAMPLE 79

100 ml of a waste catalyst solution (Rh concentrations 329 mg/l) from hydroformylation of propylene having the same composition as in Example 74, and 1,000 ml of a 1.0M/l ammonium acetate aqueous solution, were charged into a 10 l stainless steel autoclave of induction stirring type, and air was supplied and pressurized to 100 kg/cm$^2$.G, followed by treatment at 120° C. for 6 hours. Then, the temperature was lowered to room temperature, then the air was released, and the system was left to stand still, whereupon the aqueous phase was separated. As a results the extraction ratio of rhodium into the aqueous phase was 84.6%. 150 ml of this aqueous solution and 150 ml of a toluene solution containing 25% of TPP (oil/water ratio: 1/1) were charged into a 0.5 l autoclave of up and down agitating types and stirred at 130° C. for 0.5 hour under a water gas pressure of 50 kg/cm$^2$.G. After the treatments the temperature was lowered, and the system was left to stand still, whereupon the oil phase and the aqueous phase were separated. The rhodium concentrations of the respective phases were analyzed by a Zeeman atomic absorption method, and the recovery of Rh was determined in the same manner as in Example 49. As a result, the recovery of Rh was 39.1%.

To confirm that the aqueous solution after the water gas treatment can be used for recycling, a reaction solution (Rh concentration: 342.9 mg/l) of hydroformylation of propylene was added to this aqueous solution (Rh concentration: 188.0 mg/l) containing ammonium acetate after the water gas treatment in a volume ratio of 1:1, and the oxidation treatment and water gas treatment were repeated for a total of four times. The results are shown in the following Table 16 together with the results of the above first time. The oxidation treatment in the second and subsequent times was carried out by a 0.5 l autoclave of up and down agitating type.

TABLE 16

| No. | Rh concentration in the starting material (mg/l) | Oxidation extraction ratio (%) *1 | Water gas treatment recovery (%) *2 | Rh concentration in the aqueous phase after treatment (mg/l) | Toluene phase overall recovery (%) *3 |
|---|---|---|---|---|---|
| 1 | 329 | 84.6 | 39.1 | 188.0 | 33.1 |
| 2 | 342.9 | 85.3 | 30.8 | 375.4 | 44.2 |
| 3 | 342.9 | 84.6 | 37.6 | 458.8 | 71.9 |
| 4 | 342.9 | 87.6 | 38.0 | 497.2 | 75.6 |

*1: Oxidation extraction ratio = (1 − amount of Rh remaining in the oil phase after oxidation treatment/amount of Rh in the starting material) × 100
*2: Water gas treatment recovery = (amount of Rh in the toluene phase/ amount of Rh in the aqueous solution before treatment) × 100
*3: Toluene phase overall recovery = (amount of Rh in the toluene phase/ amount of Rh in the starting material) × 100

EXAMPLE 80

50 ml of a reaction solution (Rh concentration: 408.1 mg/l) of hydroformylation of propylene having the same composition as in Example 74 and 50 ml of a 1M/l sulfuric acid aqueous solution were charged into 0.5 l stainless steel autoclave of induction stirring type, and air was supplied and pressurized to 100 kg/cm$^2$.G. followed by treatment at 120° C. for 6 hours. Then, the temperature was lowered to room temperature, then the air was released, and the system was left to stand still, whereupon the aqueous phase was separated. Further, the oil phase was washed with water, and the washing water was mixed with the extracted aqueous phase. As a result, the recovery of rhodium into the aqueous phase was 89.6%. 170 ml of this aqueous solution (Rh concentration: 107.4 mg/l) and 50 ml of a toluene solution containing 25% of TPP were charged into a 0.5 l autoclave of up and down agitating type, and stirred at 130° C. for 0.5 hour under a water gas pressure of 50 kg/cm$^2$.G. After the treatment, the temperature was lowered, and the system was left to stand still, whereupon the oil phase and the aqueous phase were separated. The rhodium concentrations in the respective phases were analyzed by a Zeeman atomic absorption method, and the recovery of Rh was determined in the same manner as in Example 78. As a result, the recovery of Rh was 74.9%. Accordingly, the overall recovery of rhodium from the initial waste liquid solution from hydroformylation of propylene to the toluene solution was 67.1%.

Using this toluene solution, a hydroformylation reaction of propylene was carried out. To an autoclave of up and down agitating type, 50 ml of this solution and 10 g of propylene were charged, and the reaction was carried out at 113° C. for 2 hours under a water gas pressure of 50 kg/cm$^2$.G. As a result, the conversion of propylene was 99.2%.

As described in detail in the foregoing Examples and Comparative Examples, according to the process of the present invention, it is possible to efficiently prepare an organic solvent solution of a rhodium-tertiary organic phosphorus compound complex solution useful as a catalyst for a hydroformylation reaction, from an aqueous solution of a water-soluble rhodium compound. Especially when the process of the present invention is carried out in the presence of a $C_{2-8}$ carboxylic acid, it is possible to recover rhodium from an aqueous solution of rhodium at a recovery exceeding 99% and to obtain an organic solvent solution of a rhodium-tertiary organic phosphorus compound complex solution.

Further, by combining this process with a process for recovering rhodium into an aqueous medium from a waste catalyst solution used for a hydroformylation reaction, the obtained rhodium complex solution can be recycled for use as a catalyst for the hydroformylation reaction, whereby an aldehyde can be efficiently produced.

What is claimed is:

1. A process for preparing a rhodium complex solution, which comprises contacting an aqueous solution of a water-soluble rhodium compound and an organic solvent solution of a water-insoluble tertiary organic phosphorus compound in a gas atmosphere containing carbon monoxide, followed by two phase separation, and recovering an organic solvent phase containing a rhodium-tertiary organic phosphorus compound complex.

2. The process for preparing a rhodium complex solution according to claim 1, wherein the step of contacting an aqueous solution of a water-soluble rhodium compound and an organic solvent solution of a water-insoluble tertiary organic phosphorus compound in a gas atmosphere containing carbon monoxide, is carried out in the presence,of a $C_{2-8}$ carboxylic acid as a complexing accelerator.

3. The process for preparing a rhodium complex solution according to claim 1, wherein the water-soluble rhodium compound is an inorganic acid salt of rhodium.

4. The process for preparing a rhodium complex solution according to claim 1, wherein the water-soluble rhodium compound is a rhodium salt of a $C_{2-8}$ carboxylic acid.

5. The process for preparing a rhodium complex solution according to claim 1, wherein the aqueous solution of a water-soluble rhodium compound is a rhodium-containing aqueous solution separated from a hydroformylation react solution of an olefin.

6. The process for preparing a rhodium complex solution according to claim 5, wherein the aqueous solution of a water-soluble rhodium compound is a rhodium-containing aqueous solution obtained by treating a rhodium-containing solution separated from the hydroformylation reaction solution of an olefin, with an oxidizing agent in the presence of a recovery accelerator and an aqueous medium.

7. The process for preparing a rhodium complex solution according to claim 6, wherein the recovery accelerator is at least one member selected from the group consisting of (A) a $C_{2-8}$ carboxylic acid, (B) an amine or an amine salt ammonia or an ammonium salt, and (D) an alkali metal salt of an inorganic acid.

8. The process for preparing a rhodium complex solution according to claim 7, wherein a $C_{2-8}$ carboxylic acid is used at the recovery accelerator, and it is used also as a complexing accelerator without being removed.

9. The process for preparing a rhodium complex solution according to claim 8, wherein the carboxylic acid is acetic acid.

10. The process for preparing a rhodium complex solution according to claim 1, wherein the water-insoluble tertiary organic phosphorus compound is a triarylphosphine.

11. The process for preparing a rhodium complex solution according to claim 1, wherein the gas containing carbon monoxide is a gas mixture of hydrogen and carbon monoxide (water gas), and its pressure is within a range of atmospheric pressure to 300 kg/cm$^2$.G.

12. A process for producing an aldehyde by hydroformylating a compound having an olefinic unsaturated bond with carbon monoxide and hydrogen in the presence of a rhodium complex in a water-insoluble solvent, which comprises:

1) a waste catalyst separation step of separating a rhodium-containing liquid from a hydroformylation reaction step, 2) an oxidation/extraction step of subjecting the rhodium-containing liquid to oxidation treatment in the presence of an aqueous medium containing a recovery accelerator to extract rhodium into an aqueous phase, 3) a rhodium-containing aqueous phase separation step of separating the aqueous phase from an organic phase, 4) a complexing step of contacting the aqueous phase containing rhodium, with an organic solvent solution of a water-insoluble tertiary organic phosphorus compound, in a gas atmosphere containing carbon monoxide, to extract rhodium in the form of a tertiary organic phosphorus compound complex into the organic solvent, 5) a rhodium complex separation step of separating the organic phase from the aqueous phase, and 6) a recycling step of recycling the organic phase containing the rhodium-tertiary organic phosphorus compound complex to the above-mentioned hydroformylation step.

13. The process for producing an aldehyde according to claim 12, wherein the aqueous phase separated from the organic phase containing the rhodium-tertiary organic phosphor compound complex, is supplied to the oxidation/extraction step.

14. The process for producing an aldehyde according to claim 12, wherein the recovery accelerator is at least one member selected from the group consisting of (A) a $C_{2-4}$ carbomylic acid, (B) an amine or an amine salt, and (C) ammonia or an ammonium salt.

15. The process for producing an aldehyde according to claim 12, wherein oxygen or an oxygen-containing gas is used for the oxidation treatment in the oxidation/extraction step.

16. The process for producing an aldehyde according to claim 12, wherein the water-insoluble tertiary organic phosphorus compound used in the complexing step, is a triarylphosphine.

17. The process for producing an aldehyde according to claim 12, wherein the gas containing carbon monoxide used in the complexing step, is water gas.

18. The process for producing an aldehyde according to claim 17, wherein the pressure of the water gas is within a range of atmospheric pressure to 300 kg/cm$^2$.G.

19. A process for recovering rhodium, which comprises contacting a rhodium-containing solution used for a hydroformylation reaction, with an oxidizing agent and an aqueous medium containing at least one recovery accelerator selected from the group consisting of (A) a $C_{2-4}$ carboxylic acid, (B) an amine or an amine salt, (C) ammonia or an ammonium salt, and (D) an alkali metal salt of an inorganic acid, followed by phase separation, and recovering an aqueous phase containing rhodium.

20. The process for recovering rhodium according to claim 19, wherein the $C_{2-4}$ carboxylic acid is an aliphatic monocarboxylic acid or dicarboxylic acid.

21. The process for recovering rhodium according to claim 19, wherein the $C_{2-4}$ carboxylic acid is acetic acid.

22. The process for recovering rhodium according to claim 19, wherein the inorganic acid is at least one acid selected from the group consisting of sulfuric acid, nitric acid, hydrochloric acid, carbonic acid, phosphoric acid and, boric acid, and the alkali metal is sodium or potassium.

23. The process for recovering rhodium according to claim 19, wherein the amine is an aliphatic amine having a polar substituent.

24. The process for recovering rhodium according to claim 19, wherein the amine is a heterocyclic amine.

25. The process for recovering rhodium according to claim 19, wherein the ammonium salt is an ammonium salt of an aliphatic carboxylic acid or an aromatic carboxylic acids.

26. The process for recovering rhodium according to claim 19, wherein the ammonium salt is an ammonium salt of an inorganic acid.

27. The process for recovering rhodium according to claim 19, wherein the volume ratio of the aqueous medium to the rhodium-containing solution is from 0.1 to 10.

28. The process for recovering rhodium according to claim 19 wherein the oxidizing agent is oxygen or an oxygen-containing gas.

29. The process for recovering rhodium according to claim 19, wherein the oxidizing agent is an inorganic peroxide or organic peroxide.

30. The process for recovering rhodium according to claim 19 wherein the rhodium-containing solution used for the hydroformylation reaction, is a solution obtained by subjecting a $C_{2-20}$ olefinic hydrocarbon to hydroformylation in the presence of a rhodium complex compound and an organic phosphorus compound and then removing the majority of the aldehyde product and the organic phosphorus compound.

* * * * *